(12) United States Patent
McNally et al.

(10) Patent No.: US 10,801,029 B2
(45) Date of Patent: *Oct. 13, 2020

(54) COMPOSITIONS AND METHODS FOR CORRECTING LIMB GIRDLE MUSCULAR DYSTROPHY TYPE 2C USING EXON SKIPPING

(71) Applicants: THE UNIVERSITY OF CHICAGO, Chicago, IL (US); NORTHWESTERN UNIVERSITY, Evanston, IL (US)

(72) Inventors: Elizabeth McNally, Oak Park, IL (US); Eugene Wyatt, Chicago, IL (US)

(73) Assignees: THE UNIVERSITY OF CHICAGO, Chicago, IL (US); NORTHWESTERN UNIVERSITY, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/395,741

(22) Filed: Apr. 26, 2019

(65) Prior Publication Data
US 2019/0249180 A1    Aug. 15, 2019

Related U.S. Application Data

(63) Continuation of application No. 15/564,681, filed as application No. PCT/US2016/026477 on Apr. 7, 2016, now Pat. No. 10,273,483.
(Continued)

(51) Int. Cl.
*C12N 15/11*    (2006.01)
*A61K 48/00*    (2006.01)
(Continued)

(52) U.S. Cl.
CPC ........ *C12N 15/1138* (2013.01); *C12N 15/113* (2013.01); *C12N 2310/11* (2013.01);
(Continued)

(58) Field of Classification Search
CPC .............. C12N 15/113; C12N 15/1138; C12N 2310/11; C12N 2310/346;
(Continued)

(56) References Cited

U.S. PATENT DOCUMENTS

| 3,687,808 A | 8/1972 | Merigan, Jr. et al. |
| 4,845,205 A | 7/1989 | Huynh Dinh et al. |

(Continued)

FOREIGN PATENT DOCUMENTS

| EP | 1072679 A2 | 1/2001 |
| WO | WO-1997/012896 A1 | 4/1997 |

(Continued)

OTHER PUBLICATIONS

Echigoya and Yokota (Nucleic Acids Therapeutics, 2014 vol. 24:57-68).*

(Continued)

*Primary Examiner* — Terra C Gibbs
(74) *Attorney, Agent, or Firm* — Marshall, Gerstein & Borun LLP

(57) ABSTRACT

The invention is directed to one or more antisense polynucleotides and their use in pharmaceutical compositions in a strategy to induce exon skipping in the γ-sarcoglycan gene in patients suffering from Limb-Girdle Muscular Dystrophy-2C (LGM-D2C) or in patients at risk of such a disease. The invention also provides methods of preventing or treating muscular dystrophy. e.g., LGMD2C, by exon skipping in the gamma sarcoglycan gene using antisense polynucleotides. Accordingly, in some aspects the invention provides an isolated antisense oligonucleotide, wherein the oligonucleotide specifically hybridizes to an exon target region of a γ-sarcoglycan RNA. In another aspect, the invention provides a method of inducing exon-skipping of a gamma (Continued)

sarcoglycan RNA, comprising delivering an antisense oligonucleotide or a composition to a cell.

21 Claims, 11 Drawing Sheets

Specification includes a Sequence Listing.

Related U.S. Application Data

(60) Provisional application No. 62/144,712, filed on Apr. 8, 2015.

(51) Int. Cl.
  C07H 21/02 (2006.01)
  C07H 21/04 (2006.01)
  C12N 15/113 (2010.01)

(52) U.S. Cl.
  CPC .... C12N 2310/31 (2013.01); C12N 2310/315 (2013.01); C12N 2310/3181 (2013.01); C12N 2310/321 (2013.01); C12N 2310/3233 (2013.01); C12N 2310/346 (2013.01); C12N 2310/351 (2013.01); C12N 2310/3513 (2013.01); C12N 2310/3521 (2013.01); C12N 2320/33 (2013.01)

(58) Field of Classification Search
  CPC ...... C12N 2310/3233; C12N 2310/315; C12N 2310/321; C12N 2310/3521; C12N 2310/3515
  See application file for complete search history.

(56) References Cited

U.S. PATENT DOCUMENTS

| | | | |
|---|---|---|---|
| 5,130,302 A | 7/1992 | Spielvogel et al. | |
| 5,134,066 A | 7/1992 | Rogers et al. | |
| 5,139,941 A | 8/1992 | Muzyczka et al. | |
| 5,149,797 A | 9/1992 | Pederson et al. | |
| 5,175,273 A | 12/1992 | Bischofberger et al. | |
| 5,252,479 A | 10/1993 | Srivastava | |
| 5,328,688 A | 7/1994 | Roizman | |
| 5,367,066 A | 11/1994 | Urdea et al. | |
| 5,432,272 A | 7/1995 | Benner | |
| 5,457,187 A | 10/1995 | Gmeiner et al. | |
| 5,459,255 A | 10/1995 | Cook et al. | |
| 5,474,935 A | 12/1995 | Chatterjee et al. | |
| 5,484,908 A | 1/1996 | Froehler et al. | |
| 5,502,177 A | 3/1996 | Matteucci et al. | |
| 5,525,711 A | 6/1996 | Hawkins et al. | |
| 5,539,082 A | 7/1996 | Nielsen et al. | |
| 5,552,540 A | 9/1996 | Haralambidis | |
| 5,585,362 A | 12/1996 | Wilson et al. | |
| 5,587,469 A | 12/1996 | Cook et al. | |
| 5,594,121 A | 1/1997 | Froehler et al. | |
| 5,596,091 A | 1/1997 | Switzer | |
| 5,614,617 A | 3/1997 | Cook et al. | |
| 5,622,856 A | 4/1997 | Natsoulis | |
| 5,631,237 A | 5/1997 | Dzau et al. | |
| 5,645,985 A | 7/1997 | Froehler et al. | |
| 5,658,776 A | 8/1997 | Flotte et al. | |
| 5,661,033 A | 8/1997 | Ho et al. | |
| 5,670,488 A | 9/1997 | Gregory et al. | |
| 5,681,941 A | 10/1997 | Cook et al. | |
| 5,693,509 A | 12/1997 | Cotten et al. | |
| 5,707,618 A | 1/1998 | Armentano et al. | |
| 5,714,331 A | 2/1998 | Buchardt et al. | |
| 5,719,262 A | 2/1998 | Buchardt et al. | |
| 5,750,692 A | 5/1998 | Cook et al. | |
| 5,763,588 A | 6/1998 | Matteucci et al. | |
| 5,773,289 A | 6/1998 | Samulski et al. | |
| 5,789,390 A | 8/1998 | Descamps et al. | |
| 5,792,453 A | 8/1998 | Hammond et al. | |
| 5,824,544 A | 10/1998 | Armentano et al. | |
| 5,830,653 A | 11/1998 | Froehler et al. | |
| 5,830,727 A | 11/1998 | Wang et al. | |
| 5,834,441 A | 11/1998 | Philip et al. | |
| 5,849,571 A | 12/1998 | Glorioso et al. | |
| 5,851,521 A | 12/1998 | Branellec et al. | |
| 5,856,152 A | 1/1999 | Wilson et al. | |
| 5,863,541 A | 1/1999 | Samulski et al. | |
| 5,879,934 A | 3/1999 | DeLuca | |
| 6,005,096 A | 12/1999 | Matteucci et al. | |
| 7,223,833 B1 | 5/2007 | Nielsen et al. | |
| 8,486,907 B2 | 7/2013 | Wilton et al. | |
| 9,499,817 B2 | 11/2016 | McNally | |
| 9,777,271 B2 | 10/2017 | McNally | |
| 10,273,483 B2 * | 4/2019 | McNally | C12N 15/1138 |
| 2004/0005707 A1 | 1/2004 | Cooper et al. | |
| 2005/0100885 A1 | 5/2005 | Crooke | |
| 2008/0113351 A1 | 5/2008 | Naito et al. | |
| 2012/0149756 A1 | 6/2012 | Schumperli et al. | |
| 2018/0037889 A1 | 2/2018 | McNally | |

FOREIGN PATENT DOCUMENTS

| | | |
|---|---|---|
| WO | WO-1998/039352 A1 | 9/1998 |
| WO | WO-1999/014226 A2 | 3/1999 |
| WO | WO-2005/116204 | 12/2005 |
| WO | WO-2013/057485 A1 | 4/2013 |
| WO | WO-2014/039916 A1 | 3/2014 |
| WO | WO-2014/100714 A1 | 6/2014 |

OTHER PUBLICATIONS

Yokota et al. (Expert Opinion on Biological Therapy, 2012 vol. 12:1141-1152).*
Aartsma-Rus et al., "Overview on AON Design," Methods and Protocols, Methods in Molecular Biology, Chapter 7, 867:97-116 (2012).
Aartsma-Rus et al., "Overview on AON Design," Methods and Protocols, Methods in Molecular Biology, Chapter 8, 867:117-129 (2012).
Aartsma-Rus et al., "Therapeutic antisense-induced exon skipping in cultured muscle cells from six different DMD patients," Human Molecular Genetics 12(8):907-914 (2003).
Aartsma-Rus et al., Antisense-mediated exon skipping: a versatile tool with therapeutic and research applications, *RNA*, 13:1609-24 (2007).
Aartsma-Rus et al., Therapeutic exon skipping for dysferlinopathies?, *Euro, J. Hum. Genet.*, 18:889-94 (2010).
Allikian et al., "Reduced life span with heart and muscle dysfunction in *Drosophila sarcoglycan* mutants," Hum Mol Genet 16:2933-2943 (2007).
Allikian et al., Processing and assembly of the dystrophin glycoprotein complex, *Traffic*, 8:177-83 (2007).
Ausubel et al., Current Protocols in Molecular Biology, Greene Publishing Associates and John Wiley & Sons, New York, N.Y. (1994).
Baker et al., "Nonsense-mediated mRNA decay: terminating erroneous gene expression," Curr Opin Cell Biol 16:293-299 (2004).
Balke, "A Simple Field Test for the Assessment of Physical Fitness," Rep. Civ. Aeromed. Res. Inst. US. 53:1-8 (1963).
Bansal et al., Defective membrane repair in dysferlin-deficient muscular dystrophy, *Nature*, 423:168-72 (2003).
Barton, "Impact of sarcoglycan complex on mechanical signal transudction in murine skeletal muscle," Am J Physiol Cell Physiol 290:C411-419 (2006).
Barton, "Restoration of γ-Sarcoglycan Localization and Mechanical Signal Transduction Are Independent in Murine Skeletal Muscle," J Biol Chem 285:17263-17270 (2010).
Bertoni, Clinical approaches in the treatment of Duchenne muscular dystrophy (DMD) using oligonucleotides, *Front Biosci.*, 13:517-27 (2008).
Bonnemann et al., "β-sarcoglycan (A3b) mutations cause autosomal recessive muscular dystrophy with loss of the sarcoglycan complex," Nat Genet 11:266-273 (1995).

(56) References Cited

OTHER PUBLICATIONS

Boshart et al., "A Very Strong Enhances Is Located Upstream of an Immeidate Early Gene of Human Cytomegalovirus," Cell 41:521-530 (1985).
Brand et al., "Targeted gene expression as a means of altering cell fates and generating dominant phenotypes," Development 118:401-415 (1993).
Chan et al., "Molecular Organization of Sarcoglycan Complex in Mouse Myotubes in Culture," J Cell Biol 143:2033-2044 (1998).
Chen et al., "High-Efficiency Transformation of Mammalian Cells by Plasmid DNa," Mol. Cell Biol. 7:2745-2752 (1987).
Chen et al., "Identification of functional domains in sarcoglycans essential for their interaction and plasma membrane targeting," Exp Cell Res 312:1610-1625 (2006).
Cirak et al., "Exon skipping and dystrophin restoration in patients with Duchenne muscular dystrophy after systemic phosphorodiamidate morpholino oligomer treatment: an open-label, phase 2, dose-escalation study," Lancet 378:595-605 (2011).
Cohn et al., "Molecular Basis of Muscular Dystrophies," Muscle Nerve 23:1456-1471 (2000).
Cook, "Medicinal chemistry of antisense oligonucleotides—future opportunities," Anti-Cancer Drug Design , 6: 585-607 (1991).
Crosbie et al., Molecular and genetic characterization of sarcospan: insights into sarcoglycan-sarcospan interactions, Hum. Mol. Genet., 9:2019-27 (2000).
Curtis et al., Morphology of the pupal heart, adult heart, and associated tissues in the fruit fly, Drosophila melanogaster, Morphology, 240:225 (1999).
Davis et al., "Direct Gene Transfer into Skeletal Muscle In Vivo: Factors Affecting Efficiency of Transfer and Stability of Expression," Hum. Gene Ther., 4:151-159 (1993).
Dean, "Nonviral gene transfer to skeletal, smooth, and cardiac muscle in living animals," Am J Physiol Cell Physiol. 289(2):C233-45 (2005).
Deleavy et al., Chemical Modificaiton of SiRNA, Curr. Prot. Nuc. Acid. Chem., 39:1-22 (2009).
Doherty et al., Normal myoblast fusion requires myoferlin, Development, 132:5565-75 (2005).
Doriguzzi et al., Congenital muscular dystrophy associated with familial junctional epidermolysis bullosa letalis, Eur. Neurol., 33:454-60 (1993).
Dubowitz, Muscle disorders in childhood. Saunders, Philadelphia. xiii, 282 (1978).
Duclos et al., "Progressive Muscular Dystrophy in α-Sarcoglycan-deficient MIce," J Cell Biol 142:1461-1471 (1998).
Durbeej et al., "Disruption of the β-Sarcoglycan Gene Reveals Pathogenetic Complexity of Limb-Girdle Muscular Dystrophy Type 2E," Mol Cell 5:141-151 (2000).
Durbeej et al., "Muscular dystrophies involving the dystrophin-glycoprotein complex: an overview of current mouse models," Curr Opin Genet Dev 12:349-361 (2002).
Englisch et al., "Chemically Modified Oligonucleotides as Probes and Inhibitors," Angewandte Chemie, International Edition, 30: 613-722 (1991).
Ervasti et al., "A Role for the Dystrophin-Glycoprotein Complex as a Transmembrane Linker between Laminin and Actin," J Cell Biol 122:809-823 (1993).
Ervasti et al., "Dystrophin, its interactions with other proteins, and implications for muscular dystrophy," Cell 66:1121-1131 (1991).
Ervasti, "Dystrophin, its interactions with other proteins, and implications for muscular dystrophy," Biochim Biophys Acta 1772:108-117 (2007).
F. Eckstein (ed.) Oligonucleotides and Analogues, 1st Ed. (Oxford University Press, New York (1991).
Fechheimer et al., "Transfection of mammalian cells with plasmid DNA by scrape loading and sonication loading," Proc. Natl. Acad. Sci. USA, 84:8463-8467 (1987).
Feigner, "Improvements in Cationic Liposomes for In Vivo Gene Transfer," Hum Gene Ther. 7(15):1791-1793 (1996).
Felgner, "Nonviral Strategies for Gene Therapy," Sci Am. 276(6):102-106 (1997).
Fraley et al., "Entrapment of a bacterial plasmid in phospholipid vesicle: Potential for gene transfer," Proc. Natl. Acad. Sci. USA, 76:3348-3352 (1979).
Freier et al., "The ups and downs of nucleic acid duplex stability: structure-stability studies on chemically-modified DNA:RNA duplexes," Nucleic Acids Research, 25:4429-4443 (1997).
Gao et al., "Reengineering a transmembrane protein to treat muscular dystrophy using exon skipping," Journal of Clinical Investigation, 125(11):4186-4195 (2015).
Gnatenko et al., "Characterization of Recombinant Adeno-Associated Virus-2 as a Vehicle for Gene Delivery and Expression into Vascular Cells," J. Invest. Med., 45:87-98 (1997).
Goemans et al., "Systemic Administration of PRO051 in Duchenne's Muscular Dystrophy," The New England Journal of Medicine 364:1513-1522 (2011).
Goldstein et al., "Excess SMAD signaling contributes to heart and muscle dysfunction in muscular dystrophy," Hum Mol Genet 23:6722-6731 (2014).
Goldstein et al., Mechanisms of muscle weakness in muscular dystrophy, J. Gen. Physiol., 136: 29-34 (2010).
Goldstein et al., SMAD signaling drives heart and muscle dysfunction in a Drosophila model of muscular dystrophy, Hum. Mol. Genet., 20:894-904 (2011).
Gopal, "Gene Transfer Method for Transient Gene Expression, Stable Transformation, and Cotransformation of Suspension Cell Cultures," Mol. Cell Biol. 5:1188-1190 (1985).
Goyenvalle et al. "Functional correction in mouse models of muscular dystrophy using exon-skipping tricyclo-DNA oligomers," Nature Medicine 21(3): 270-275 (2015).
Graham et al., "A New Technique for the Assay of Infectivity of Human Adenovirus 5 DNA," Virology 52:456-467 (1973).
Hack et al., "Differential requirement for individual sarcoglycans and dystrophin in the assembly and function of the dystrophin-glycoprotein complex," J Cell Sci 113:2535-2544 (2000).
Hack et al., "γ-Sarcoglycan Deficiency Leads to Muscle Membrane Defects and Apoptosis Independent of Dystrophin," J Cell Biol 142:1279-1287 (1998).
Harland, et al., "Translation of mRNA Injected into Xenopus Oocytes Is Specifically Inhibited by Antisense RNA," J. Cell Biol. 101:1094-1099 (1985).
Henricson et al., "The 6-Minute Walk Test and Person-Reported Outcomes in Boys with Duchenne Muscular Dystrophy and Typically Developing Controls: Longitudinal Comparisons and Clinically-Meaningful Changes Over One Year," PLoS Currents 8(5):1-20 (2013).
Herson et al., "A phase I trial of adeno-associated virus serotype 1—sarcoglycan gene therapy for limb girdle muscular dystrophy type 2c," Brain 135:483-492 (2012).
Heydemann et al., "Genetic background influences muscular dystrophy," Neuromuscul Disord 15:601-609 (2005).
Heydemann et al., Latent TGF-beta-binding protein 4 modifies muscular dystrophy in mice, J. Clin. Invest., 119(12):3703-12 (2009).
Hoffman, et al., Dystrophin: the protein product of the Duchene muscular dystrophy locus. 1987, Biotechnology, 24: 457-66 (1992).
Honda et al., Specific knockdown of delta-sarcoglycan gene in C2C12 in vitro causes post-translational loss of other sarcoglycans without mechanical stress, Mol. Cell. Biochem., 323(1-2):149-59 (2009).
International Preliminary Report on Patentability from PCT/US2016/026477 dated Oct. 10, 2017.
International Search Report and Written Opinion from PCT/US2016/026477 dated Jul. 8, 2016.
International Search Report and Written Opinion of the International Searching Authority, PCT/US2013/058636, dated Jan. 16, 2014.
Isner et al., "Arterial Gene Therapy for Therapeutic Angiogenesis in Patients with Peripheral Artery Disease," Circulation 91:2687-2692 (1995).
Isner et al., "Clinical Protocol—Arterial Gene Therapy for Restenosis," Human Gene Therapy, 7:989-1011 (1996).

(56) References Cited

OTHER PUBLICATIONS

Ittig et al, "Position-dependent effects on stability in tricyclo-DNA modified oligonucleotide duplexes," Nucleic Acids Research 39(1):373-380 (2011).
Katz, "The Reversible Reaction of Sodium Thymonucleate and Mercuric Chloride," J. Am. Chem. Soc., 74:2238-2245 (1952).
Kaufman et al., "Electroporation- and Mechanical Ventilation-Mediated Gene Transfer to the Lung," Gene Ther. 17(9):1098-1104 (2010).
Kendall et al., "Dantroene Enhances Antisense-Mediated Exon Skipping in Human and Mouse Models of Duchenne Muscular Dystrophy," Science Translational Medicine 4:164ra160, 1-13 (2012).
Kim et al., "Minimal Requirement for a Lentivirus Vector Based on Human Immunodeficiency Virus Type 1," J. Virol. 72(1):811-816 (1998).
Kimura et al., "Cell-lineage regulated myogenesis for dystrophin replacement: a novel therapeutic approach for treatment of muscular dystrophy," Hum Mol Genet 17:2507-2517 (2008).
Kinali et al., "Local restoration of dystrophin expression with the morphilino oligomer AVI-4658 in Duchenne muscular dystrophy: a single-blind, placebo-controlled, dose-escalation, proof-of-concept study," Lancet Neurol 8:918-928 (2009).
Kingsman et al., "A new generation of gene therapy vectors," Scrip Magazine pp. 43-46 (1998).
Klein et al., "High-velocity microprojectiles for delivering nucleic acids into living cells," Nature 327:70-73 (1987).
Kosturko et al., "The Crystal and Molecular Structure of a 2:1 Complex of 1-Methylthymine-Mercury (II)," Biochemistry 13:3949-3952 (1974).
Kroschwitz (ed.), The Concise Encyclopedia of Polymer Science and Engineering, pp. 858-859, John Wiley & Sons, (1990).
Lasa et al., Severe limb girdle muscular dystrophy in Spanish gypsies: further evidence for a founder mutation in the gamma-sarcoglycan gene, Eur. J. Hum. Genet., 6:396-9 (1998).
Lattanzi et al., High efficiency myogenic conversion of human fibroblasts by adenoviral vector-mediated MyoD gene transfer. An alternative strategy for ex vivo gene therapy of primary myopathies, J. Clin. Invest., 101:2119-28 (1998).
Lehner et al., "Comparative Sequence Analysis of Human Cytomegalovirus Strains," J. Clin. Microbiol. 29:2494-2502 (1991).
Li et al., Inhibition of desmin expression blocks myoblast fusion and interferes with the myogenic regulators MyoD and myogenin, J. Cell Biol., 124:827-41 (1994).
Liu et al., RNAi-based Gene Therapy for Dominant Limb Girdle Muscular Dystrophies, Curr. Gene Ther., 12(4):307-14 (2012).
Lo et al., "A role for the COUP-TF-related gene seven-up in the diversification of cardioblast identities in the dorsal vessel of Drosophila," Mech Dev 104:49-60 (2001).
Lu et al., "What Can We Learn From Clinical Trials on Exon Skipping for DMD?", Mol Ther Nucleic Acids 3:e152 (2014).
Magnusson et al., "Sustained, high transgene expression in liver with plasmid vectors using optimized promoter-enhancer combinations," J Gene Med. 13(7-8): 382-91 (2011).
Martin, Remington's Pharmaceutical Sciences, 18th Ed., Mack Publishing Co., Easton, Pa., (1990).
Matsuda et al., Visualization of dystrophic muscle fibers in mdx mouse by vital staining with Evans blue: evidence of apoptosis in dystrophin-deficient muscle, J. Biochem., 118:959-64 (1995).
McNally et al., "Mild and Severe Muscular Dystrophy Caused by a Single γ-Sarcoglycan Mutation," Am J Hum Genet 59:1040-1047 (1996).
McNally et al., "Mutations that disrupt the carboxyl-terminus of γ-sarcoglycan cause muscular dystrophy," Hum Mol Genet 5:1841-1847 (1996).
Mizuno et al., "Selective Defect of Sarcoglycan Complex in Severe Childhood Autosomal Recessive Muscular Dystrophy Muscle," Biochem Biophys Res Commun 203:979-983 (1994).
Moorwood et al., "Absence of γ-sarcoglycan alters the response of p70S6 kinase to mechanical perturbation in murine skeletal muscle," Skeletal Muscle 4:13, pp. 1-13 (2014).

Moser, Duchenne muscular dystrophy: pathogenetic aspects and genetic prevention, Hum. Genet., 66:17-40 (1984).
Nicolau et al., "Liposome-Mediated DNA Transfer in Eukaryotic Cells—Dependence of the Transfer Efficiency Upon the Type of Liposomes Used and the ost Cell Cycle Stage," Biochim. Biophys. Acta, 721:185-190, (1982).
Nielsen et al., "Sequence-Selective Recognition of DNA by Strand Displacement with a Thymine-Substituted Polyamide," Science 254:1497-1500 (1991).
Nigro et al., "Autosomal recessive limb-girdle muscular dystrophy, LGMD2F, is caused by a mutation in the δ-sarcoglycan gene," Nat Genet 14:195-198 (1996).
Noguchi et al., "Formation of sarcoglycan complex with differentiation in cultured myocytes," Eur J Biochem 267:640-648 (2000).
Noguchi et al., "Mutations in the Dystrophin-Associated Protein γ-Sarcoglycan in Chromosome 13 Muscular Dystrophy," Science 270:819-822 (1995).
Ohlendieck et al., "Dystrophin-associated Proteins are Greatly Reduced in Skeletal Muscle from mdx Mice," J Cell Biol 115:1685-1694 (1991).
Ohlendieck et al., Dystrophin-glycoprotein complex is highly enriched in isolated skeletal muscle sarcolemma, J. Cell Biol., 112:135-48 (1991).
Ozawa et al., "Molecular and Cell Biology of the Sarcoglycan Complex," Muscle Nerve 32:563-576 (2005).
Pacak et al., "Tissue specific promoters improve specificity of AAV9 mediated transgene expression following intra-vascular gene delivery in neonatal mice," Genet Vaccines Ther 6:13, pp. 1-5 (2008).
Passos-Bueno et al., Half the dystrophin gene is apparently enough for a mild clinical course: confirmation of its potential use for gene therapy, Hum. Mol. Genet., 3:919-22 (1994).
Piccolo et al., "A founder mutation in the γ-sarcoglycan gene of Gypsies possibly predating their migration out of India," Hum Mol Genet 5:2019-2022 (1996).
Potter et al., "Enhancer-dependent expression of human κ immunoglobulin genes introduced into mouse pre-B lymphocytes by electroporation," Proc. Nat. Acad. Sci. USA, 81: 7161-7165 (1984).
Quantin et al., "Adenovirus as an expression vector in muscle cells in vivo," Proc. Natl. Acad. Sci. USA, 89:2581-2584 (1992).
Rahimov et al., "Cellular and molecular mechanisms underlying muscular dystrophy," J Cell Biol 201: 499-510 (2013).
Ranganayakulu et al., "Wingless Signaling Induces nautilus Expression in the Ventral Mesoderm of the Drosophila Embryo," Dev Biol 176:143-148 (1996).
Rippe et al., "DNA-Mediated Gene Transfer into Adult Rat Hepatocytes in Primary Culture," Mol. Cell Biol. 10:689-695 (1990).
Roberds et al., "Missense Mutations in the Adhalin Gene Linked to Autosomal recessive Muscular Dystrophy," Cell 78:625-633 (1994).
Rosenfeld et al., "In Vivo Transfer of the Human Cystic Fibrosis Transmembrane Conductance Regulator Gene to the Airway Epithelium," Cell, 68:143-155 (1992).
Sambrook et al., Molecular Cloning: A Laboratory Manual (2nd ed. 1989).
Sandona et al. "Sarcoglycanopathies: molecular pathogenesis and therapeutic prospects," 11(1):1-27 (2009).
Sanghvi, Y. S., Chapter 15, Antisense Research and Applications, pp. 274-288, Crooke, S. T. and Lebleu, B., ed., CRC Press (1993).
Schuster et al., "Genetic Dissection of Structural and Functional Components of Synaptic Plasticity. I. Fasciclin II Controls Synaptic Stabilization and Growth," Neuron 17:641-654 (1996).
Search Report from European Application No. 13835266.1 dated May 20, 2016.
Shcherbata et al., Dissecting muscle and neuronal disorders in a Drosophila model of muscular dystrophy, EMBO J., 26:481-93 (2007).
Shi et al., "Specific Assembly Pathway of Sarcoglycans is Dependent on Beta- and Delta-Sarcoglycan," Muscle Nerve 29:409-419 (2004).
Spinazzola et al., "Gamma-sarcoglycan is required for the response of archvillin to mechanical stimulation in skeletal muscle," Hum Mol Genet 24(9):2470-2481 (2015).

(56) References Cited

OTHER PUBLICATIONS

Stratford Perricaudet et al., "Widespread Long-term Gene Transfer to Mouse Skeletal Muscles and Heart," J. Clin. Invest. 90:626-630 (1992).
Su et al., A gene atlas of the mouse and human protein-encoding transcriptomes, *Proc. Natl. Acad. Sci. USA*, 101:6062-7 (2004).
Swaggart et al., Distinct genetic regions modify specific muscle groups in muscular dystrophy, *Physiol. Genomics*, 43(1):24-31 (2011).
The Concise Encyclopedia of Polymer Science and Engineering, pp. 858-859, Kroschwitz, J. I., ed. John Wiley & Sons (1990).
Thomas, "The Interaction of $HgCl_2$ with Sodium Thymonucleate," J. Am. Chem. Soc., 76:6032-6034 (1954).
Thompson et al., "Filamin 2 (FLN2): A Muscle-specific Sarcoglycan Interacting Protein," J Cell Biol 148:115-126 (2000).
Tur-Kaspa et al., "Use of Electroporation to Introduce Biologically Active Foreign Genes into Primary Rat Hepatocytes," Mol. Cell Biol. 6:716-718 (1986).
Vainzof et al., "The sarcoglycan complex in the six autosomal recessive limb-girdle muscular dystrophies," Hum Mol Genet 5:1963-1969 (1996).
van Deutekom et al., "Local Dystrophin Restoration with Antisense Oligonucleotide PRO051," The New England Journal of Medicine 357:2677-2686 (2007).
van Roon-Mom et al., "Overview on Applications of Antisense-Mediated Exon Skipping," Methods Mol Biol., Chapter 6, 867:79-96 (2012).
Wang et al., "Successful Regional Delivery and Long-term Expression of a Dystrophin Gene in Canine Muscular Dystrophy: A Preclinical Model for Human Therapies," Mol Ther. 20(8):1501-1507 (2012).
Weintraub et al., The myoD gene family: nodal point during specification of the muscle cell lineage, *Science*, 251:761-6 (1991).
Wolf et al., "*Drosophila melanogaster* as a model system for genetics of postnatal cardiac function," Drug Discov Today Dis Models 5:117-123 (2008).
Wolf et al., *Drosophila* as a model for the identification of genes causing adult human heart disease, *Proc. Natl. Acad. Sci. USA.*, 103:1394-9 (2006).
Wu et al., "Evidence for Targeted Gene Delivery to Hep G2 Hepatoma Cells in Vitro," Biochemistry, 27:887-892 (1988).
Wu et al., "Liver-directed gene delivery," Adv. Drug Delivery Rev., 12:159-167 (1993).
Wu et al., "Receptor-mediated in Vitro Gene Transformation by a Soluble DNA Carrier System," J. Biol. Chem 262:4429-4432 (1987).
Yamane et al., "On the Complexing of Desoxyribonucleic Acid (DNA) by Mercuric Ion," J. Am. Chem. Soc., 83:2599-2607 (1961).
Yang et al., "In vivo and in vitro gene transfer to mammalian somatic cells by particle bombardment," Proc. Natl. Acad. Sci USA 87:9568-9572 (1990).
Yoshida et al., "Bidirectional Signaling between Sarcoglycans and the Integrin Adhesion System in Cultured L6 Myocytes," J Biol Chem 273:1583-1590 (1998).
Zhang et al., "An extremely stable and orthogonal DNA base pair with a simplified three-carbon backbone," J. Am. Chem. Soc., 127:74-75 (2005).
Zhang et al., "Dual AAV therapy ameliorates exercise-induced muscle injury and functional ischemia in murine models of Duchenne muscular dystrophy," Hum Mol Genet. 22(18):3720-3729 (2013).
Zhu et al., "Cardiomyopathy is independent of skeletal muscle disease in muscular dystrophy," FASEB J., 16:1096-8 (2002).
Zimmermann, et al., "A Novel Silver(I)-Mediated DNA Base Pair," J. Am. Chem. Soc., 124:13684-13685 (2002).
International Preliminary Report on Patentability, PCT/US2013/058636, dated Mar. 10, 2015.

* cited by examiner

A. Multi-exon skipping in LGMD2C

B. Multi-exon skipping restores reading frame in LGMD 2C

COMPOSITIONS AND METHODS FOR CORRECTING LIMB GIRDLE MUSCULAR DYSTROPHY TYPE 2C USING EXON SKIPPING

CROSS REFERENCE TO RELATED APPLICATIONS

This application is a Continuation of U.S. application Ser. No. 15/564,681, filed Oct. 5, 2017, which is a U.S. National Phase of PCT/US2016/026477, filed Apr. 7, 2016, which claims the priority benefit under 35 U.S.C. § 119(e) of U.S. Provisional Patent Application No. 62/144,712, filed Apr. 8, 2015, which are incorporated herein by reference in their entirety.

STATEMENT OF GOVERNMENT INTEREST

This invention was made with government support under Grant Number HL061322 awarded by the National Institutes of Health. The government has certain rights in the invention.

FIELD OF THE INVENTION

The present disclosure relates to antisense polynucleotides and their use in pharmaceutical compositions to induce exon skipping in targeted exons of the gamma sarcoglycan gene (γ-sarcoglycan; SGCG), useful in treating various forms of Muscular Dystrophy.

INCORPORATION BY REFERENCE

Incorporated by reference in its entirety is a computer-readable nucleotide/amino acid sequence listing submitted concurrently herewith and identified as follows: ASCII text file named "49246A_SeqListing.txt,"; 8,129 bytes; created Apr. 6, 2016.

BACKGROUND OF THE INVENTION

Mutations that disrupt the dystrophin glycoprotein complex (DGC) cause muscular dystrophy [Durbeej et al., Curr Opin Genet Dev 12: 349-361 (2002); Ervasti, Biochim Biophys Acta 1772: 108-117 (2007); Rahimov et al., J Cell Biol 201: 499-510 (2013)]. Dystrophin and its associated proteins localize to the muscle plasma membrane, acting as a linker between the intracellular cytoskeleton to the extracellular matrix [Ervasti et al., J Cell Biol 122: 809-823 (1993); Cohn et al., Muscle Nerve 23: 1456-1471 (2000)]. Large deletions in the dystrophin gene account for Duchenne muscular dystrophy (DMD), and those mutations that maintain the reading frame of dystrophin cause the milder Becker muscular dystrophy (BMD). This observation has been the basis for developing antisense sequences that will induce additional exon skipping events and restore reading frame. Exon skipping, by design, generates an internally truncated and partially functional protein. Clinical trials that test exon skipping in DMD are advancing [Kinali et al., Lancet Neurol 8: 918-928 (2009); Cirak et al., Lancet 378: 595-605 (2011); van Deutekom et al., The New England Journal of Medicine 357: 2677-2686 (2007); Goemans et al., The New England Journal of Medicine 364: 1513-1522 (2011); Lu et al., Mol Ther Nucleic Acids 3: e152 (2014)].

In heart and muscle, the sarcoglycan subcomplex within the DGC is composed of four single pass transmembrane subunits: α, β, γ, and δ-sarcoglycan [Ervasti et al., Cell 66: 1121-1131 (1991); Ozawa et al., Muscle Nerve 32: 563-576 (2005)]. Loss-of-function mutations in genes encoding α, β, γ, and δ-sarcoglycan cause the Limb Girdle Muscular Dystrophies type 2E, 2F, 2C, 2D, respectively [Roberds et al., Cell 78: 625-633 (1994); Bonnemann et al., Nat Genet 11: 266-273 (1995); Noguchi et al., Science 270: 819-822 (1995); Nigro et al., Nat Genet 14: 195-198 (1996)].

SUMMARY OF THE INVENTION

The disclosure is directed to one or more antisense polynucleotides and their use in pharmaceutical compositions in a strategy to induce exon skipping in the γ-sarcoglycan gene in patients suffering from Limb-Girdle Muscular Dystrophy-2C (i.e., LGMD2C) or in patients at risk of such a disease. The disclosure also provides methods of preventing or treating muscular dystrophy, e.g., LGMD2C, by exon skipping in the gamma sarcoglycan gene using antisense polynucleotides.

Accordingly, in some aspects the disclosure provides an isolated antisense oligonucleotide (AON) wherein the oligonucleotide specifically hybridizes to an exon target region of a γ-sarcoglycan RNA, wherein the AON is selected from the group consisting of oligonucleotides listed in Table 2. In some aspects, the disclosure provides an isolated antisense oligonucleotide (AON) selected from the group consisting of oligonucleotides listed in Table 2. In further aspects, the disclosure provides a composition comprising one or more distinct antisense oligonucleotides (AONs) listed in Table 2. In still further aspects, the disclosure provides an isolated antisense oligonucleotide (AON) comprising a sequence as set out in Table 2. In some embodiments, the oligonucleotide cannot form an RNase H substrate.

In further embodiments, the antisense oligonucleotide comprises a modified oligonucleotide backbone, while in still further embodiments the modified oligonucleotide backbone comprises a modified moiety substituted for the sugar of at least one of the oligonucleotides. In some embodiments, the modified moiety is a Morpholino.

The disclosure also provides embodiments in which the modified oligonucleotide backbone of at least one of the oligonucleotides comprises at least one modified internucleotide linkage. In some embodiments, the modified internucleotide linkage is a tricyclo-DNA (tc-DNA) modification. In further embodiments, the modified internucleotide linkage comprises a modified phosphate. In still further embodiments, the modified phosphate is selected from the group consisting of a methyl phosphonate, a methyl phosphorothioate, a phosphoromorpholidate, a phosphoropiperazidate and a phosphoroamidate.

In some embodiments, the oligonucleotide is a 2'-O-methyl-oligoribonucleotide. In further embodiments, the oligonucleotide comprises a peptide nucleic acid.

Also provided by the disclosure are embodiments wherein the oligonucleotide is chemically linked to one or more conjugates that enhance the activity, cellular distribution, or cellular uptake of the antisense oligonucleotide. In some embodiments, the oligonucleotide is chemically linked to a polyethylene glycol molecule. In further embodiments, the conjugate is a peptide that enhances cellular uptake. Regarding the peptide, the disclosure provides embodiments wherein the peptide is selected from the group consisting of a nuclear localization signal (NLS), HIV-1 TAT protein, a peptide comprising an integrin binding domain, oligolysine, adenovirus fiber protein and a peptide comprising a receptor-mediated endocytosis (RME) domain.

In further aspects of the disclosure, a pharmaceutical composition is provided comprising an antisense oligonucleotide of the disclosure and a physiologically compatible buffer.

In another aspect, the disclosure provides a method of inducing exon-skipping of a gamma sarcoglycan RNA, comprising delivering to a cell an antisense oligonucleotide or a composition of the disclosure, thereby inducing exon-skipping of the gamma sarcoglycan RNA. In some embodiments, the cell is a human muscle cell (i.e., a skeletal muscle fiber). In further embodiments, the human muscle cell is in a patient, and in still further embodiments the patient has muscular dystrophy. In some embodiments, the muscular dystrophy is Limb Girdle Muscular Dystrophy type 2C (LGMD2C).

In some aspects, the disclosure provides a method of ameliorating Limb Girdle Muscular Dystrophy type 2C (LGMD2C) in a patient in need thereof comprising the step of administering to the patient a therapeutically effective amount of a composition of the disclosure, thereby ameliorating LGMD2C.

In another aspect, a method of inhibiting the progression of dystrophic pathology associated with LGMD2C in a patient in need thereof is provided, comprising the step of administering to the patient a therapeutically effective amount of a composition of the disclosure, thereby inhibiting the progression of dystrophic pathology.

In some aspects, the disclosure provides a method of improving muscle function in a patient suffering from Limb Girdle Muscular Dystrophy type 2C (LGMD2C) comprising the step of administering to the patient a therapeutically effective amount of a composition of the disclosure, thereby improving muscle function. In some embodiments, the muscle is a cardiac muscle.

In further embodiments, the improvement in muscle function is an improvement in muscle strength. In some embodiments, the improvement in muscle strength is an improvement in respiratory muscle strength.

The disclosure further provides embodiments, in which the improvement in muscle function is an improvement in motor stability, improved upper limb strength, or improved cardiac function. In some embodiments, the improvement in motor stability results in an improved six-minute walk test by the patient relative to a previously measured six-minute walk test by that patient. In further embodiments, the improvement in motor stability results in improved exercise endurance.

In further aspects, the disclosure provides a kit comprising an antisense oligonucleotide of the disclosure, optionally in a container, and a package insert, package label, instructions or other labeling. In some embodiments, the kit further comprises an additional oligonucleotide, wherein the additional oligonucleotide specifically hybridizes to an exon in a gamma sarcoglycan RNA.

Another aspect of the disclosure is drawn to a kit comprising the antisense polynucleotides as described herein, optionally in a container, and a package insert, package label, instructions or other labeling. In some embodiments, the kit further comprises an additional polynucleotide, wherein the additional polynucleotide specifically hybridizes to an exon in a gamma sarcoglycan RNA.

Additional aspects and embodiments of the disclosure are described in the following enumerated paragraphs.

DETAILED DESCRIPTION OF THE INVENTION

Figure 1:
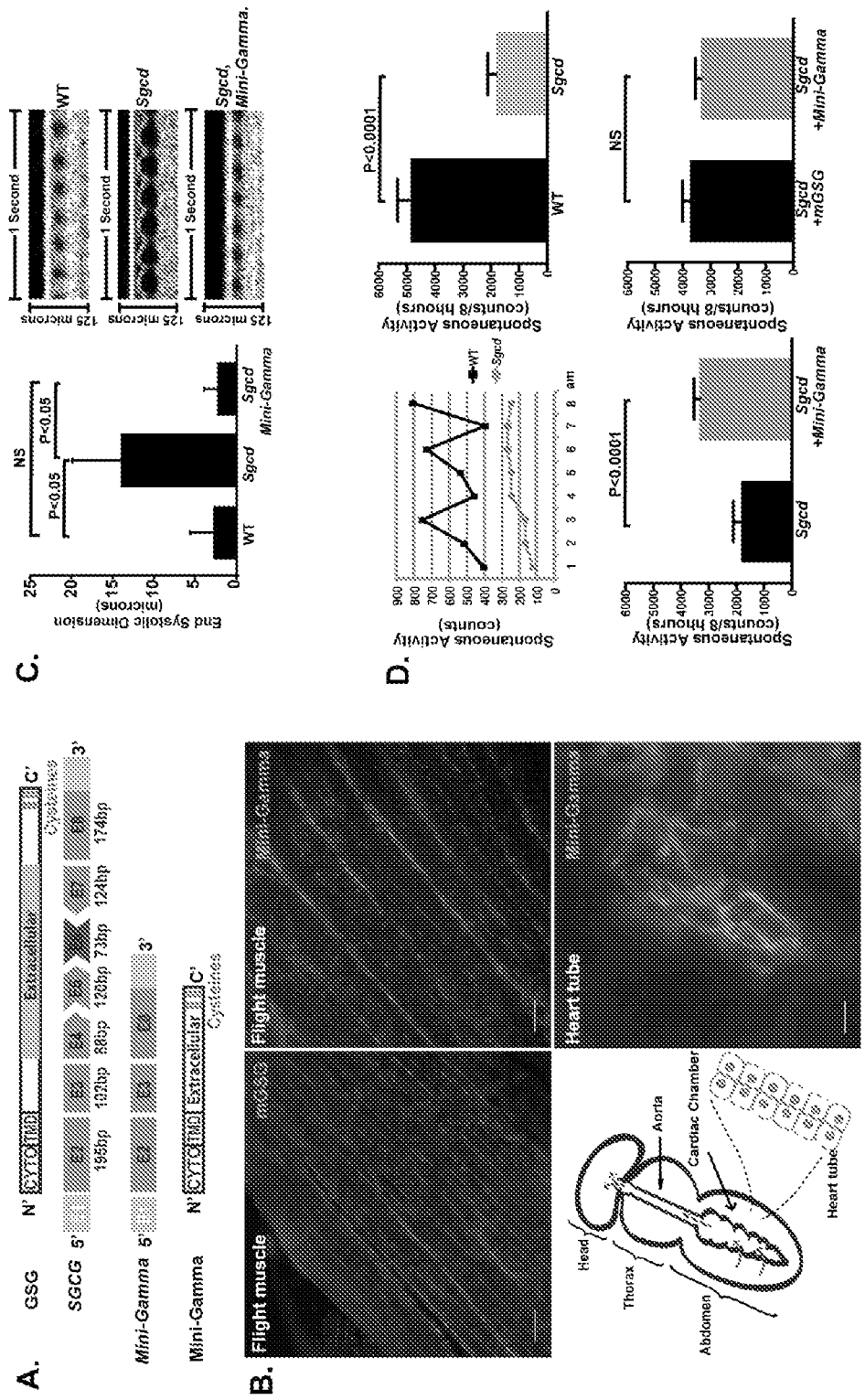
FIG. 1 shows that Mini-Gamma rescued *Drosophila* muscular dystrophy. A. γ-sarcoglycan (GSG) is a type 2 transmembrane protein with a cytoplasmic amino-terminus and extracellular carboxy-terminus. The SGCG gene encoding γ-sarcoglycan is composed of 8 exons, and the most common mutation falls within exon 6 and disrupts the reading frame [Noguchi et al., Science 270: 819-822 (1995)]. To restore the reading frame, skipping exons 4, 5, 6, and 7 is required. This approach removes a portion of the extracellular domain, producing an internally truncated protein, referred to as Mini-Gamma. B. The UAS-Gal4 system was used to express full length murine γ-sarcoglycan, referred to as mGSG or Mini-Gamma as transgene in Sgcd840 flies, a sarcoglycan deficient model of muscular dystrophy. mGSG protein localized to the plasma membrane in Sgcd840 fly skeletal muscle (Mef-Gal4, UAS-Mini-Gamma), similar to full-length murine γ-sarcoglycan (Mhc-Gal4, UAS-mGSG). In fly heart tube, Mini-Gamma also showed plasma membrane staining (TinC-Gal4, UAS-Mini-Gamma). Scale bar=20 μm. C. Optical coherence tomography (OCT) was used to measure fly heart function [Wolf et al., Drug Discov Today Dis Models 5: 117-123 (2008)]. Sgcd840 flies had dilated heart tubes with increased end systolic dimension (ESD) compared to wildtype flies. Expression of Mini-Gamma in the Sgcd840 heart tube restored ESD to wild type level (Mef-Gal4, UAS-Mini-Gamma) (n=10-12 flies per genotype.) D. MB5 monitor was used to record fly spontaneous activity and nocturnal activity is shown (12 AM to 8 AM). Expression of Mini-Gamma improved nocturnal activity of Sgcd840. The degree of rescue was similar to between mGSG and Mini-Gamma (n=20-35 flies per genotype.)

The present disclosure demonstrates the application of an exon skipping strategy to treat LGMD 2C patients with mutations in SGCG, the gene encoding γ-sarcoglycan. The most common mutation in LGMD2C patients is a deletion of a thymine from a string of 5 thymines at 521-525 base pair (bp) in exon 6 of the γ-sarcoglycan gene, referred to as 521ΔT. This mutation shifts the reading frame and results in the absence of γ-sarcoglycan protein and secondary reduction of γ- and δ-sarcoglycan [Noguchi et al., Science 270: 819-822 (1995)]. To skip this mutation and restore reading frame requires skipping of exons 4, 5, 6 and 7 together. This internally truncated protein, which we refer to as "Mini-Gamma," retains the intracellular, transmembrane and extreme carboxy-terminus. See FIG. 1.

In some aspects, the disclosure provides one or more isolated antisense oligonucleotide(s) wherein the one or more oligonucleotide(s) specifically hybridizes to an exon target region of a γ-sarcoglycan RNA. In various embodiments, the AON is selected from the group consisting of oligonucleotides listed in Table 2. In any of the aspects or embodiments of the disclosure, it is specifically contemplated that the complement of any of the antisense oligonucleotide sequences disclosed herein is utilized in a method or composition of the disclosure.

In any of the aspects or embodiments disclosed herein, the disclosure also contemplates use of an antisense oligonucleotide that is at least about 70% identical to an antisense oligonucleotide disclosed herein. In further embodiments, an antisense oligonucleotide that is at least about 75%, or at least about 80%, or at least about 85%, or at least about 90%, or at least about 95%, or is 99% identical to an antisense oligonucleotide disclosed herein is contemplated for use.

As used herein, "hybridization" means an interaction between two or three strands of nucleic acids by hydrogen bonds in accordance with the rules of Watson-Crick DNA complementarity, Hoogstein binding, or other sequence-specific binding known in the art. Hybridization can be performed under different stringency conditions known in the art. "Specifically hybridize," as used herein, is hybridization that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex" has 19 base pairs. The remaining bases may, for example, exist as 5' and/or 3' overhangs. Further, within the duplex, 100% complementarity is not required; substantial complementarity is allowable within a duplex. Substantial complementarity refers, in various embodiments, to 75%, 80%, 85%, 90%, 95%, 99% or 100% complementarity. For example, a mismatch in a duplex consisting of 19 base pairs results in 94.7% complementarity, rendering the duplex substantially complementary. In general, an antisense oligonucleotide (AON) "having substantial complementarity" to an exon is one that is sufficiently complementary to an exon against which it is directed to bind to and effect skipping of the exon.

It is noted here that, as used in this specification and the appended claims, the singular forms "a," "an," and "the" include plural reference unless the context clearly dictates otherwise.

It is also noted that the term "about" as used herein is understood to mean approximately.

The terms "polynucleotide" and "oligonucleotide" are used interchangeably herein.

As used herein, the term "ameliorating" takes on its standard meaning in the art, where it is understood to mean "to make better or more tolerable." Thus, "ameliorating Limb Girdle Muscular Dystrophy" would include but not be limited to improving or making more tolerable the disease, as would be understood in the art, or to improving or making more tolerable one or more symptoms of Limb Girdle Muscular Dystrophy, such as by reducing the severity of any deleterious symptom including weakness that affects the skeletal muscles including the upper and lower limbs as to affect walking and/or activities of daily living, exercise endurance, cardiac muscle dysfunction, respiratory muscle weakness, and serum and urine biomarkers of cardiac and skeletal muscle breakdown.

Antisense Polynucleotides/Polynucleotide Design

According to a first aspect of the invention, there is provided an antisense polynucleotide capable of binding to a selected target to induce exon skipping. To induce exon skipping in exons of the γ-sarcoglycan gene (SGCG) transcript, the antisense polynucleotide is selected based on the exon sequences shown in Tables 1 and 2. The disclosure also provides a combination or "cocktail" of two or more antisense polynucleotides capable of binding to a selected target or targets to induce exon skipping. The exon skipping contemplated herein induces exclusion of exons 4, 5, 6, and/or 7 so as to generate an in-frame, internally truncated γ-sarcoglycan protein. Excluding exons 4, 5, 6 and 7 results in the generation of an internally truncated protein lacking 135 amino acids, while deleting exon 5 results in an internally deleted, in-frame protein lacking 40 amino acids. The internally truncated proteins, termed mini-Gamma, retains the capacity to interact with dystrophin and its associated proteins and stabilize cardiac and skeletal muscle cells.

Within the context of the disclosure, preferred target site(s) are those involved in mRNA splicing (i.e., splice donor sites, splice acceptor sites or exonic splicing enhancer elements). Splicing branch points and exon recognition sequences or splice enhancers are also potential target sites for modulation of mRNA splicing.

Thus, in various embodiments, one, two three, four, five, six, seven, eight, nine, ten, eleven, twelve, thirteen, fourteen, fifteen or more antisense polynucleotides are used to induce exon skipping of a gamma sarcoglycan nucleic acid. The choice of the number of antisense polynucleotides can be determined empirically by one of ordinary skill in the art. The person of ordinary skill can individually test the relative ability of compositions comprising one, two three, four or more antisense polynucleotides to produce a protein product of interest in vitro. Briefly, and in one specific embodiment, a composition comprising a single antisense polynucleotide that is designed to specifically hybridize (i.e., block) a splice acceptor site in exon 4 of a gamma sarcoglycan nucleic acid is added to a culture of fibroblasts obtained from a patient harboring a mutation in SGCG. Next, the fibroblasts are induced to adopt a myogenic lineage via forced MyoD expression (see Example 2 for details), and the resulting myotubes are tested for surface expression of a Mini-Sgcg protein via, for example and without limitation, an immunofluorescence experiment. Further immunofluorescence microscopy analysis of the myotubes can be conducted to identify whether additional sarcoglycans (i.e., α-, β- and δ-sarcoglycan) are co-localized with Mini-Gamma in myotubes. Such co-localization of the members of the sarcoglycan complex associated with muscle membranes indicates that the Mini-Gamma that is produced following administration of the composition comprising a single antisense polynucleotide is able to effectively induce exon skipping of the SGCG-encoded nucleic acid to result in a truncated protein that retained its ability to associate with the other members of the sarcoglycan complex, as well as embed in a muscle membrane. Similar experiments may be conducted with compositions that individually comprise two, three, four, five or more antisense polynucleotides, each designed to specifically hybridize to an exon of a SGCG-encoded nucleic acid.

To identify and select antisense polynucleotides suitable for use in the modulation of exon skipping, a nucleic acid sequence whose function is to be modulated must first be identified. This may be, for example, a gene (or mRNA transcribed form the gene) whose expression is associated with a particular disorder or disease state, or a nucleic acid molecule from an infectious agent. Within the context of the disclosure, suitable target site(s) are those involved in mRNA splicing (e.g., splice donor sites, splice acceptor sites, or exonic splicing enhancer elements). Splicing branch points and exon recognition sequences or splice enhancers are also potential target sites for modulation of mRNA splicing contemplated by the disclosure.

TABLE 1

Table of exon coordinates based on the UCSC Human Genome Build 19.

| | exon start | exon end | exon start + 30 | exon end + 30 |
|---|---|---|---|---|
| exon 4 | 23824768 | 23824856 | 23824738 | 23824886 |
| exon 5 | 23853497 | 23853617 | 23853467 | 23853647 |
| exon 6 | 23869553 | 23869626 | 23869523 | 23869656 |
| exon 7 | 23894775 | 23894899 | 23894725* | 23894929 |

Sgcg exons per UCSC hg19, transcript NM_000231
*50 from exon start because of T rich region Those of skill in the art can readily design antisense polynucleotides according to the present disclosure. For example, general teachings in the art include, but are not limited to, Aartsma-Rus et al., Methods Mol Biol. 867: 117-29 (2012); Aartsma-Rus et al., Methods Mol Biol. 867: 97-116 (2012); van Roon-Mom et al., Methods Mol Biol. 867: 79-96 (2012), each of which is incorporated herein by reference. General guidelines also include attempting to avoid 3 consecutive G or C nucleotides, choosing lengths and sequences that favor self structure (hairpinning will be avoided), and avoiding those sequences likely to form primer dimers. In some embodiments, an antisense polynucleotide of the disclosure is one that is designed to specifically hybridize to an exon or an intron-exon boundary, such that the antisense polynucleotide specifically hybridizes to a sequence that is completely within an exon of a gamma sarcoglycan nucleic acid, or about one nucleotide of the antisense polynucleotide spans said intron-exon boundary when the antisense polynucleotide is specifically hybridized to the SGCG-encoded nucleic acid. In some embodiments wherein the antisense polynucleotide specifically hybridizes to a sequence that is completely within an exon, it is contemplated that a terminus of the antisense polynucleotide is about 1, 2, 3, 4, 5, 6, 7, 8, 9, 10 or more nucleotides from a terminus of the exon. The intron-exon boundary for each of exons 4, 5, 6, and 7 is shown in Table 1. In further embodiments, an antisense polynucleotide of the disclosure is one that is designed to specifically hybridize to an intron-exon boundary of a SGCG-encoded nucleic acid, such that about 2, 3, 4, 5, 6, 7, 8, 9, 10 or more nucleotides of the antisense polynucleotide span said intron-exon boundary. It is understood that a nucleotide can "span the intron-exon boundary" on either the exon side or intron side. Thus, an antisense polynucleotide that specifically and predominantly hybridizes to intronic sequence and only hybridizes to one nucleotide of an adjoining exon would "span the intron-exon boundary" by one nucleotide. Similarly, an antisense polynucleotide that specifically hybridizes to exonic sequence and only hybridizes to one nucleotide of an adjoining intron would "span the intron-exon boundary" by one nucleotide. In any of the aforementioned embodiments, the antisense polynucleotide is at least about 10 nucleotides and up to about 15, 20, 25, 30, 35, 40, 45, 50 or more nucleotides in length. Lengths of antisense polynucleotides contemplated by the disclosure are discussed in more detail below.

Specific antisense oligonucleotides (AONs) contemplated by the disclosure include, but are not limited to, the oligonucleotides listed in Table 2, below.

In some aspects, the disclosure provides pharmaceutical compositions comprising an antisense polynucleotide to induce exon skipping of a SGCG-encoded nucleic acid, such that a "Mini-Gamma" protein is produced that has the ability to (a) effectively associate with other members of the sarcoglycan complex (i.e., α-, β- and δ-sarcoglycan) and (b) correctly embed in a muscle membrane. In some embodiments, methods described herein result in the restoration of a sarcoglycan at a muscle membrane surface, such that about 1% of the gamma sarcoglycan protein is restored relative to the amount of γ-sarcoglycan protein at a muscle membrane in the absence of administration of the pharmaceutical composition. In further embodiments, methods described herein result in the restoration of a sarcoglycan protein at the muscle membrane surface, such that about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 2-fold, about 3-fold, about 4-fold, about 5-fold, about 6-fold, about 7-fold, about 8-fold, about 9-fold, about 10-fold or more of the gamma sarcoglycan protein is restored relative to the amount of γ-sarcoglycan protein at the muscle membrane in the absence of administration of the pharmaceutical composition. Such restoration of γ-sarcoglycan protein at the muscle membrane can be determined by one of ordinary skill in the art by, for example and without limitation, obtaining a muscle biopsy from the patient and performing immunofluorescence with an antibody that has specific binding affinity for Mini-Gamma protein.

In any of the aspects or embodiments of the disclosure, it is contemplated that the individual genotype of the patient will determine the antisense oligonucleotide(s) to be administered. Thus, in various embodiments a patient harbors a deletion of one or more exons of the SGCG gene. In other embodiments, a patient harbors one or more mutations within an exon of the SGCG gene.

Accordingly, in some embodiments the genotype of the patient is evaluated to determine whether the patient harbors a deletion of one or more exons of the SGCG gene. If a deletion of one or more exons of the SGCG gene is detected in the patient, then one or more AON(s) are administered to the patient to target the exons that are retained in the patient. Thus, in some embodiments the goal is to skip one of exons 4, 5, 6, or 7, and only one AON is administered to a patient to effect single exon skipping. In further embodiments, it is contemplated that more than one exon is skipped, and in such embodiments 2, 3, 4, 5, 6, 7, 8, 9, 10, or more AONs are administered to a patient to effect multiple exon skipping. Thus, the disclosure contemplates compositions comprising at least two oligonucleotides listed in Table 2. In various embodiments, the one or more AONs administered to a patient are selected from the group consisting of oligonucleotides listed in Table 2.

In some embodiments, the patient harbors a mutation in exon 6, and the patient is administered an AON selected from the group of oligonucleotides listed in Table 2 to target exons 4, 5 and 7.

In further embodiments, the patient harbors a mutation in exon 7 and the patient is administered an AON selected from the group of oligonucleotides listed in Table 2 to target exons 4, 5 and 6.

As described above, and in further embodiments, the patient harbors one or more mutations within exons of SGCG including small deletions/insertions, transitions, or transversions that create an altered reading frame or dysfunctional γ-sarcoglycan protein by substituting amino acids other than the conventional γ-sarcoglycan protein. In an embodiment, a patient harbors a mutation in exon 4, and AONs are administered to target exons 5, 6, and 7, and another AON having substantial complementarity to the precise mutation in exon 4 is administered. In an embodiment, the patient harbors a mutation in exon 5 and AONs are administered to target exons 4, 6, and 7 and another AON having substantial complementarity to the precise mutation in exon 5 is administered. In some embodiments, the patient harbors a mutation in exon 6 and AONs are administered to target exons 4, 5, and 7 and another AON having substantial complementarity to the precise mutation within exon 6 is administered. In further embodiments, the patient harbors a mutation in exon 7 and the patient is administered a single AON to skip exons 4, 5, 6 and another AON having substantial complementarity to the precise mutation in exon 7 is administered.

In some embodiments, the patient harbors the 521ΔT mutation in exon 6 and AONs are administered to target exons 4, 5, and 7 and an AON having substantial complementarity to the 521ΔT mutation within exon 6 is administered. In some embodiments, the patient harboring the 521ΔT mutation in exon 6 is administered AONs having sequences as set out in SEQ ID NOs: 20, 21, 24 and 25.

Polynucleotides

Products, uses and methods of the disclosure comprise one or more polynucleotides. As used herein, a "polynucleotide" is an oligomer comprised of nucleotides. A polynucleotide may be comprised of DNA, RNA modified forms thereof, or a combination thereof.

The term "nucleotide" or its plural as used herein is interchangeable with modified forms as discussed herein and otherwise known in the art. In certain instances, the art uses the term "nucleobase" which embraces naturally occurring nucleotides as well as modifications of nucleotides that can be polymerized. Thus, nucleotide or nucleobase means the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-($C_3$-$C_6$)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which is hereby incorporated by reference in its entirety). In various aspects, polynucleotides also include one or more "nucleosidic bases" or "base units" which include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include pyrrole, and diazole or triazole derivatives, including those universal bases known in the art.

Polynucleotides may also include modified nucleobases. A "modified base" is understood in the art to be one that can pair with a natural base (e.g., adenine, guanine, cytosine, uracil, and/or thymine) and/or can pair with a non-naturally occurring base. Exemplary modified bases are described in EP 1 072 679 and WO 97/12896, the disclosures of which are incorporated herein by reference. Modified nucleobases include, without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2 (3H)-one), G-clamps such as a substituted phenoxazine cytidine (e.g. 9-(2-aminoethoxy)-H-pyrimido[5,4-b][1,4] benzox-azin-2(3H)-one), carbazole cytidine (2H-pyrimido [4,5-b]indol-2-one), pyridoindole cytidine (H-pyrido[3',2':4, 5]pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyri-done. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity of the polynucleotide and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects, combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Modified polynucleotides are contemplated for use wherein both one or more sugar and/or one or more internucleotide linkage of the nucleotide units in the polynucleotide is replaced with "non-naturally occurring" sugars (i.e., sugars other than ribose or deoxyribose) or internucleotide linkages, respectively. In one aspect, this embodiment contemplates a peptide nucleic acid (PNA). In PNA compounds, the sugar-backbone of a polynucleotide is replaced with an amide-containing (e.g., peptide bonds between N-(2-aminoethyl)-glycine units) backbone. See, for example U.S. Pat. Nos. 5,539,082; 5,714,331; and 5,719,262, and Nielsen et al., Science, 1991, 254, 1497-1500, the disclosures of which are herein incorporated by reference.

Modified polynucleotides may also contain one or more substituted sugar groups. In one aspect, a modification of the sugar includes Locked Nucleic Acids (LNAs) in which the 2'-hydroxyl group is linked to the 3' or 4' carbon atom of the sugar ring, thereby forming a bicyclic sugar group. The linkage is in certain aspects a methylene ($-CH_2-$)$_n$ group bridging the 2' oxygen atom and the 4' carbon atom wherein n is 1 or 2. LNAs and preparation thereof are described in WO 98/39352 and WO 99/14226, the disclosures of which are incorporated herein by reference.

To avoid degradation of pre-mRNA during duplex formation with the antisense polynucleotides, the antisense polynucleotides used in the method may be adapted to minimize or prevent cleavage by endogenous RNase H. This property is advantageous because the treatment of the RNA with the unmethylated polynucleotides either intracellularly or in crude extracts that contain RNase H leads to degradation of the pre-mRNA:antisense polynucleotide duplexes. Any form of modified antisense polynucleotide that is resistant to such degradation, or does not induce such degradation, is contemplated by the disclosure. Non-limiting examples of antisense molecules which, when duplexed with RNA, are not cleaved by cellular RNase H are polynucleotides comprising 2'-O-methyl derivatives of nucleotides. 2'-O-methyl-oligoribonucleotides are very stable in a cellular environment and in animal tissues, and their duplexes with RNA have higher $T_m$ values than their ribo- or deoxyribo-counterparts.

Antisense polynucleotides that do not activate RNase H can be made in accordance with known techniques (see, for example and without limitation, U.S. Pat. No. 5,149,797).

Such antisense polynucleotides, which may be deoxyribonucleotide or ribonucleotide sequences, simply contain any structural modification which sterically hinders or prevents binding of RNase H to a duplex molecule containing the polynucleotide as one member thereof, which structural modification does not substantially hinder or disrupt duplex formation. Because the portions of the polynucleotide involved in duplex formation are substantially different from those portions involved in RNase H binding thereto, numerous antisense molecules that do not activate RNase H are available. (Activation is used in this sense to refer to RNase H degradation, whether as a result of a substrate not being susceptible to such degradation or such substrate failing to induce degradation.) For example, such antisense molecules may be polynucleotides wherein at least one, or all, of the inter-nucleotide bridging phosphate residues are modified phosphates, such as methyl phosphonates, methyl phosphorothioates, phosphoromorpholidates, phosphoropiperazidates and/or phosphoramidates. For example, every other one of the internucleotide bridging phosphate residues may be modified as described. In another non-limiting example, such antisense polynucleotides are polynucleotides wherein at least one, or all, of the nucleotides contain a 2' carbon bound to a lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described.

In some embodiments, the modified internucleotide linkage is a tricyclo-DNA (tc-DNA) modification. Tc-DNA is described, e.g., in U.S. Patent Publication Number 2012/0149756, Ittig et al. [Nucleic Acids Research 39(1): 373-380 (2011)], and Goyenvalle et al. [Nature Medicine 21(3): 270-275 (2015], which are incorporated by reference herein in their entireties.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

Polynucleotides contemplated herein range from about 5 nucleotides to about 50 nucleotides in length. In some embodiments, the polynucleotide is between at least 5 nucleotides and at least 20 nucleotides, between at least 5 nucleotides and at least 30 nucleotides or between at least 5 nucleotides and at least 50 nucleotides.

In further embodiments, a polynucleotide contemplated by the disclosure is about 5 to about 60, 70, 80, 90, 100 or more nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

The polynucleotides of the disclosure are approximately 40% GC to about 60% GC, with a $T_m$ of about 48° C. or higher.

Another modification of the polynucleotides of the invention involves chemically linking the polynucleotide to one or more moieties or conjugates that enhance the activity, cellular distribution or cellular uptake of the polynucleotide. Such moieties include, but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Therapeutic Agents

The compounds of the disclosure also can be used as a prophylactic or therapeutic, which may be utilized for the purpose of treatment of a genetic disease.

In one embodiment the disclosure provides antisense polynucleotides that bind to a selected target in the SGCG-encoded pre-mRNA to induce efficient and consistent exon skipping described herein in a therapeutically or prophylactically effective amount admixed with a pharmaceutically acceptable carrier, diluent, or excipient.

A pharmaceutically acceptable carrier refers, generally, to materials that are suitable for administration to a subject wherein the carrier is not biologically harmful, or otherwise, causes undesirable effects. Such carriers are typically inert ingredients of a medicament. Typically a carrier is administered to a subject along with an active ingredient without causing any undesirable biological effects or interacting in a deleterious manner with any of the other components of a pharmaceutical composition in which it is contained. Suitable pharmaceutical carriers are described in Martin, Remington's Pharmaceutical Sciences, 18th Ed., Mack Publishing Co., Easton, Pa., (1990), incorporated by reference herein in its entirety.

In a more specific form of the disclosure there are provided pharmaceutical compositions comprising therapeutically effective amounts of an antisense polynucleotide together with pharmaceutically acceptable diluents, preservatives, solubilizers, emulsifiers, adjuvants and/or carriers. Such compositions include diluents of various buffer content (e.g., phosphate, Tris-HCl, acetate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as, for example and without limitation, polylactic acid or polyglycolic acid, or into liposomes. Hylauronic acid may also be used. Such compositions may influence the physical state, stability, rate of in vivo release, and rate of in vivo clearance of the disclosed compositions. The compositions may be prepared in liquid form, or may be in dried powder, such as lyophilized form.

It will be appreciated that pharmaceutical compositions provided according to the disclosure may be administered by any means known in the art. Preferably, the pharmaceutical compositions for administration are administered by injection, orally, or by the pulmonary, or nasal route. The antisense polynucleotides are, in various embodiments, delivered by intravenous, intra-arterial, intraperitoneal, intramuscular, or subcutaneous routes of administration.

The antisense molecules of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For polynucleotides, preferred examples of pharmaceutically acceptable salts include, but are not limited to, (a) salts formed with cations such as sodium, potassium, ammonium, magnesium, calcium, polyamines such as spermine and spermidine; (b) acid addition salts formed with inorganic acids, for example hydrochloric acid, hydrobromic acid, sulfuric acid, phosphoric acid, nitric acid; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid; and (d) salts formed from elemental anions such as chlorine, bromine, and iodine. The pharmaceutical compositions of the disclosure may be administered in a number of ways depending upon whether local or systemic treatment is desired and upon the area to be treated. Administration may be topical (including ophthalmic and to mucous membranes including rectal delivery), pulmonary, e.g., by inhalation of powders or aerosols, (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Polynucleotides with at least one 2'-O-methoxyethyl modification are believed to be particularly useful for oral administration.

The pharmaceutical formulations of the disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly bringing into association the active ingredients with liquid carriers or finely divided solid carriers or both, and then, if necessary, shaping the product.

Combination therapy with an additional therapeutic agent is also contemplated by the disclosure. Examples of therapeutic agents that may be delivered concomitantly with a composition of the disclosure include, without limitation, a glucocorticoid steroid (for example and without limitation, prednisone and deflazacort), an angiotensin converting enzyme inhibitor, a beta adrenergic receptor blocker, an anti-fibrotic agent and a combination thereof.

Gene Therapy

In some aspects, the disclosure provides methods of expressing a Mini-Gamma sarcoglycan in a cell. In any of the aspects or embodiments of the disclosure, the cell is a mammalian cell. In any of the aspects or embodiments of the disclosure, the cell is in a human and the human is in need of the Mini-Gamma sarcoglycan. Accordingly, in some aspects the disclosure provides gene therapy methods for expressing a Mini-Gamma sarcoglycan in a cell.

In some embodiments, a vector (e.g., an expression vector) comprising a polynucleotide of the invention to direct expression of the polynucleotide in a suitable host cell. Such vectors are useful, e.g., for amplifying the polynucleotides in host cells to create useful quantities thereof, and for expressing proteins using recombinant techniques. In some embodiments, the vector is an expression vector wherein a polynucleotide of the invention is operatively linked to a polynucleotide comprising an expression control sequence. Autonomously replicating recombinant expression constructs such as plasmid and viral DNA vectors incorporating polynucleotides of the disclosure are specifically contemplated. Expression control DNA sequences include promoters, enhancers, and operators, and are generally selected based on the expression systems in which the expression construct is to be utilized. In some embodiments, promoter and enhancer sequences are selected for the ability to increase gene expression, while operator sequences may be selected for the ability to regulate gene expression. Expression constructs of the invention may also include sequences encoding one or more selectable markers that permit identification of host cells bearing the construct. Expression constructs may also include sequences that facilitate, and preferably promote, homologous recombination in a host cell. Expression constructs of the disclosure also include, in various embodiments, sequences necessary for replication in a host cell.

Exemplary expression control sequences include promoter/enhancer sequences, e.g., cytomegalovirus promoter/enhancer [Lehner et al., J. Clin. Microbiol., 29: 2494-2502, 1991; Boshart et al., Cell, 41: 521-530, (1985)]; Rous sarcoma virus promoter [Davis et al., Hum. Gene Ther., 4: 151, (1993)]; and simian virus 40 promoter, for expression in a target mammalian cell, the promoter being operatively linked upstream (i.e., 5') of the polypeptide coding sequence (the disclosures of the cited references are incorporated herein by reference in their entirety and particularly with respect to the discussion of expression control sequences). In another variation, the promoter is a muscle-specific promoter. The polynucleotides of the invention may also optionally include a suitable polyadenylation sequence (e.g., the SV40 or human growth hormone gene polyadenylation sequence) operably linked downstream (i.e., 3') of the polypeptide coding sequence.

If desired, a polynucleotide of the disclosure also optionally comprises a nucleotide sequence encoding a secretory signal peptide fused in frame with the polypeptide sequence. The secretory signal peptide directs secretion of the polypeptide of the invention by the cells that express the polynucleotide, and is cleaved by the cell from the secreted polypeptide. The polynucleotide may further optionally comprise sequences whose only intended function is to facilitate large scale production of the vector, e.g., in bacteria, such as a bacterial origin of replication and a sequence encoding a selectable marker. However, if the vector is administered to an animal, such extraneous sequences are preferably at least partially cleaved. One can manufacture and administer polynucleotides for gene therapy using procedures that have been described in the literature for other transgenes. See, e.g., Isner et al., Circulation, 91: 2687-2692, 1995; Isner et al., Human Gene Therapy, 7: 989-1011, 1996; Wang et al., Mol Ther. 20(8):1501-7 (2012); and Zhang et al., Hum Mol Genet. 22(18): 3720-9 (2013); each of which is incorporated herein by reference in its entirety.

In some embodiments, a "naked" transgene encoding Mini-Gamma as described herein (i.e., a transgene without a viral, liposomal, or other vector to facilitate transfection) is employed.

Vectors also are useful for "gene therapy" treatment regimens, wherein, for example, a polynucleotide encoding a Mini-Gamma is introduced into a subject suffering from or at risk of suffering from a muscular dystrophy in a form that causes cells in the subject to express the Mini-Gamma in vivo. Any suitable vector may be used to introduce a polynucleotide that encodes a Mini-Gamma into the host. Exemplary vectors that have been described in the literature include replication deficient retroviral vectors, including but not limited to lentivirus vectors [Kim et al., J. Virol., 72(1): 811-816, (1998); Kingsman & Johnson, Scrip Magazine, October, 1998, pp. 43-46]; parvoviral vectors, such as adeno-associated viral (AAV) vectors [U.S. Pat. Nos. 5,474,9351; 5,139,941; 5,622,856; 5,658,776; 5,773,289; 5,789,390; 5,834,441; 5,863,541; 5,851,521; 5,252,479; Gnatenko et al., J. Invest. Med., 45: 87-98, (1997)]; adenoviral (AV) vectors [U.S. Pat. Nos. 5,792,453; 5,824,544; 5,707,618; 5,693,509; 5,670,488; 5,585,362; Quantin et al., Proc. Natl. Acad. Sci. USA, 89: 2581-2584, (1992); Stratford Perricaudet et al., J. Clin. Invest., 90: 626-630, (1992); and Rosenfeld et al., Cell, 68: 143-155, (1992)]; an adenoviral adeno-associated viral chimeric [U.S. Pat. No. 5,856,152] or a vaccinia viral or a herpesviral vector [U.S. Pat. Nos. 5,879,934; 5,849,571; 5,830,727; 5,661,033; 5,328,688]; Lipofectin mediated gene transfer (BRL); liposomal vectors [U.S. Pat. No. 5,631,237]; and combinations thereof. Additionally contemplated by the disclosure for introducing a polynucleotide encoding a Mini-Gamma into a subject is a plasmid vector [see, e.g., Dean, Am J Physiol Cell Physiol. 289(2): C233-45 (2005); Kaufman et al., Gene Ther. 17(9): 1098-104 (2010); Magnusson et al., J Gene Med. 13(7-8): 382-91 (2011)]. For example and without limitation, any pBR- or pUC-derived plasmid vector is contemplated. All of the foregoing documents are incorporated herein by reference in their entirety and particularly with respect to their discussion of expression vectors. Any of these expression vectors can be prepared using standard recombinant DNA techniques described in, e.g., Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994). Optionally, the viral vector is rendered replication-deficient by, e.g., deleting or disrupting select genes required for viral replication.

Other non-viral delivery mechanisms contemplated include calcium phosphate precipitation [Graham and Van Der Eb, Virology, 52: 456-467, 1973; Chen and Okayama, Mol. Cell Biol., 7: 2745-2752, (1987); Rippe et al., Mol. Cell Biol., 10: 689-695, (1990)], DEAE-dextran [Gopal, Mol. Cell Biol., 5: 1188-1190, (1985)], electroporation [Tur-Kaspa et al., Mol. Cell Biol., 6: 716-718, (1986); Potter et al., Proc. Nat. Acad. Sci. USA, 81: 7161-7165, (1984)], direct microinjection [Harland and Weintraub, J. Cell Biol., 101: 1094-1099, (1985)], DNA-loaded liposomes [Nicolau and Sene, Biochim. Biophys. Acta, 721: 185-190, (1982); Fraley et al., Proc. Natl. Acad. Sci. USA, 76: 3348-3352, (1979); Felgner, Sci Am., 276(6): 102-6, (1997); Felgner, Hum Gene Ther., 7(15): 1791-3, (1996)], cell sonication [Fechheimer et al., Proc. Natl. Acad. Sci. USA, 84: 8463-8467, (1987)], gene bombardment using high velocity microprojectiles [Yang et al., Proc. Natl. Acad. Sci USA, 87: 9568-9572, (1990)], and receptor-mediated transfection [Wu and Wu, J. Biol. Chem., 262: 4429-4432, (1987); Wu and Wu, Biochemistry, 27: 887-892, (1988); Wu and Wu, Adv. Drug Delivery Rev., 12: 159-167, (1993)].

The expression vector (or the Mini-Gamma sarcoglycan discussed herein) may be entrapped in a liposome.

In some embodiments, transferring a naked DNA expression construct into cells is accomplished using particle bombardment, which depends on the ability to accelerate DNA coated microprojectiles to a high velocity allowing them to pierce cell membranes and enter cells without killing them [Klein et al., Nature, 327: 70-73, (1987)]. Several devices for accelerating small particles have been developed. One such device relies on a high voltage discharge to generate an electrical current, which in turn provides the motive force [Yang et al., Proc. Natl. Acad. Sci USA, 87: 9568-9572, (1990)]. The microprojectiles used have consisted of biologically inert substances such as tungsten or gold beads.

In embodiments employing a viral vector, preferred polynucleotides still include a suitable promoter and polyadenylation sequence as described above. Moreover, it will be readily apparent that, in these embodiments, the polynucleotide further includes vector polynucleotide sequences (e.g., adenoviral polynucleotide sequences) operably connected to the sequence encoding a polypeptide of the disclosure.

The disclosure further provides a cell that comprises the polynucleotide or the vector, e.g., the cell is transformed or transfected with a polynucleotide encoding a Mini-Gamma sarcoglycan of the disclosure or the cell is transformed or transfected with a vector comprising a polynucleotide encoding the Mini-Gamma sarcoglycan.

Polynucleotides of the disclosure may be introduced into the host cell as part of a circular plasmid, or as linear DNA comprising an isolated protein coding region or a viral vector. Methods for introducing DNA into the host cell, which are well known and routinely practiced in the art, include transformation, transfection, electroporation, nuclear injection, or fusion with carriers such as liposomes, micelles, ghost cells, and protoplasts. As stated above, such host cells are useful for amplifying the polynucleotides and also for expressing the polypeptides of the invention encoded by the polynucleotide. The host cell may be isolated and/or purified. The host cell also may be a cell transformed in vivo to cause transient or permanent expression of the polypeptide in vivo. The host cell may also be an isolated cell transformed ex vivo and introduced post-transformation, e.g., to produce the polypeptide in vivo for therapeutic purposes.

Therapeutic Endpoints

The disclosure provides aspects in which a patient experiences an inhibition in the progression of a dystrophic pathology. The inhibition in the progression of the dystrophic pathology is understood to be relative to a patient that was not exposed to a composition and/or method of the disclosure. In some embodiments, such an inhibition in the progression of the pathology manifests as an improvement in muscle function, an improvement in muscle strength, improvement in motor stability, or improvement in cardiac and/or respiratory function.

Improvements in muscle function and in muscle strength are routinely measured by clinicians in the art. Such tests include, but are not limited to, physical examinations by medical professionals to assess general muscle tone, function and stability, serum creatine kinase content or other muscle protein fragments including titin, myosin light chain, carbonic anhydrase to measure leakage of the enzyme from damaged muscle, muscle biopsies, Computed Tomography scans (CT scans), Magnetic Resonance Imaging scans (MRIs), as well as determination of cardiac function through cardiac MRI measurements of strain, dimension, and delayed enhancement, and breathing measured by pulmonary function testing, oximetry and $CO_2$ content.

Improvements in motor stability are also routinely measured by clinicians in the art. Such improvements are measured by, inter alia, an improved six-minute walk test by the patient relative to a previously measured six-minute walk test. The test was first reported by Balke, Rep. Civ. Aeromed. Res. Inst. US. 53:1-8 1963, and its use has been developed to assess the physical condition of muscular dystrophy patients [Henricson et al., PLoS Currents 8(5): 1-20 (2013)].

Kits

The disclosure also provides kits for treatment of a patient with a genetic disease such as LGMD2C. In one aspect, the kit comprises an antisense polynucleotide as disclosed herein, optionally in a container, and a package insert, package label, instructions or other labeling.

In a further embodiment, a kit is provided that comprises an additional polynucleotide, wherein the additional polynucleotide specifically hybridizes to an exon in a gamma sarcoglycan RNA.

Those of ordinary skill in the art will appreciate that applications of the above method has wide application for identifying antisense molecules suitable for use in the treatment of many other diseases.

EXAMPLES

To assess Mini-Gamma's capacity to substitute for full-length γ-sarcoglycan, both transgenic flies and mice expressing Mini-Gamma were studied, finding functional and molecular evidence for rescue. Also provided is proof-of-principle evidence that exon skipping can be induced in SGCG mutant human cells.

The Examples below utilize the following methods.

Methods

Plasmids.
Murine Sgcg and Mini-Gamma were ligated into pUAST vector 17, and an Xpress epitope tag was added. The pUAST-Mini-Gamma was digested and inserted into pcDNA3.0 vector at EcoR1 and Xho1 sites to generate plasmids for expression in HEK cells. Mouse Sgcb (MR204617) and mouse Sgcd (MR221060) cDNA ORF clones were purchased from OriGene (Rockville, Md.). Both vectors contain CMV promoters and Myc-DDK tags at the C-terminus of the respective sarcoglycan protein.

The coding region of murine Sgcg was amplified from mouse cDNA and cloned into pUAST vector at the Xho1 and Xba1 sites [Brand et al., Development 118: 401-415 (1993)]. To generate the Mini-Gamma construct, Sgcg exons 2 and exon 3 were amplified separately from exon 8. Both PCR products were digested with BsiHKA1 and then ligated. The ligation product was introduced into pCR2.1-TOPO via TA cloning. The product was sequenced. Sequencing revealed a G to A transition at the 4th nucleotide in exon 8, resulting in a valine to isoleucine alteration. However this variant was present in all clones and represented a polymorphism in mice. The start codon and Xpress tag were filled in by Klenow DNA polymerase and inserted into pUAST vector at the EcoR1 and Not1 sites. Xpress protein tag consists of eight amino acids: DLYDDDDK. The Mini-Gamma sequence was then ligated into pUAST-Xpress. The pUAST-Mini-Gamma was digested and inserted into pcDNA3.0 vector at EcoR1 and Xho1 sites to generate PCMV-Mini-Gamma for expression in cells.

Drosophila Strains.
pUAST-Sgcg and pUAST-Mini-Gamma plasmids were integrated using P-element insertion (Rainbow Transgenics, Camarillo, Calif.). Founder males were mated to y[1]w[1118] (yw) females, and their progeny were screened for the presence of w[+mC]. The TinCΔ4-Gal4 strain was a gift from Manfred Frasch [Lo et al., Mech Dev 104: 49-60 (2001)]. Mef2-Gal4 and MHC-Gal4 were gifts from Ron Dubreuil [Ranganayakulu et al., Dev Biol 176: 143-148 (1996); Schuster et al., Neuron 17: 641-654 (1996)]. The Sgcd840 strain was previously described [Allikian et al., Hum Mol Genet 16: 2933-2943 (2007)]. The Drosophila strain y[1]w[1118] (yw) was used as the wild type control in all studies (Bloomington Stock Center, Bloomington, Ind.). Sgcd840 strain and all transgenic fly strains were backcrossed with the yw strain for 6 generations to allow homogenization across the whole genome.

Drosophila Breeding and Husbandry.
Flies were raised on standard medium at 25° C. with 12 hours light/dark cycling. To express murine Sgcg in Sgcd840 mutants, Sgcd840 allele (on X chromosome) and Mef2-Gal4 transgene (on chromosome 3) were first recombined into one fly strain Sgcd840; Mef2-Gal4. Sgcd840; Mef2-Gal4 virgin females were collected and mated with either UAS-Sgcg or UAS-Mini-Gamma males. Since Sgcd840 allele is on the X chromosome, all male progeny from this cross was null for fly Sgcd and expressed either murine full-length γ-sarcoglycan or Mini-Gamma in muscle. Five to 15 males were collected upon eclosion every day over the course of 3 to 7 days. Flies were flipped into fresh vials every three days during the aging process. yw and Sgcd840 males were collected at the same time and aged in the same manner.

Drosophila Activity Assay.
The MB5 MultiBeam Activity Monitor (TriKinetics, Waltham, Mass.) was used to quantify fly basal activity, and all activity assays were performed on flies that had been aged to 20 days after eclosion. After anesthetization by $CO_2$, individual flies were loaded into single glass tubes. One end of the glass tube was dipped in standard fly food and further sealed with a rubber cap. The other end of the glass tube was loosely sealed to allow ready air transfer. Sixteen flies were evaluated for activity in independent tubes simultaneously by monitoring infrared beam breaks. The DAMSystemMB 106X software was used to record activity at 1-minute intervals over 24-48 hours, and the DAMFileScan 108X was used to verify and process raw data (Trikinetics). Prism (Graphpad, San Diego, Calif.) was used for data analysis. Student's t-test was used to compare results between two groups.

Optical Coherence Tomography (OCT).

OCT was performed as previously described [Wolf et al., Drug Discov Today Dis Models 5: 117-123 (2008)]. Ten to twelve male flies from each group were assessed at 7 days after eclosion. The end-systolic and end-diastolic diameters for individual fly were entered into Prism (Graphpad, San Diego, Calif.). One-way analysis of variance with a post hoc Tukey test was used to compare among multiple groups.

Generation of Mini-Gamma Transgenic Mice and Mouse Breeding.

The desmin (Des) promoter was amplified from human genomic DNA to obtain the short promoter previously characterized by [Pacak et al., Genet Vaccines Ther 6: 13 (2008)]. The Des promoter sequence was then inserted into the CMV-Mini-Gamma vector at SpeI and EcoR1 sites, replacing the CMV promoter while keeping the start codon, the Xpress tag and Mini-Gamma coding sequence intact. The Des-Mini-Gamma sequence was amplified and introduced into pCR2.1-TOPO via TA cloning, then digested at the BamH1 and Not1 sites. The sequence was verified by Sanger sequencing. The digestion product was purified and injected into C57BU6J embryos at the University of Chicago Transgenic Core. Founders were screened by PCR on genomic DNA isolated from tail clippings. Two transgenic lines were established and maintained as heterozygotes. The primers used for genotyping were mini-Forward: 5'-CGAATTCACCATGGATCTGTACGACGA-3' (SEQ ID NO: 1) and mini-Reverse: 5'-CTAGATGCATGCTCGAGT-CAAAGACAG-3' (SEQ ID NO: 2). Transgenic positive animals show a single band at 530 bp. The targeted deletion to generate a null mutation of Sgcg was previously described [Hack et al., J Cell Biol 142: 1279-1287 (1998)], and this allele was previously bred through more than ten generations into C57BL/6J 48. The Des-Mini-Gamma transgene mice were bred to Sgcg null mice in the C57BL/6J background. Transgenic positive Sgcg null mice and transgenic negative Sgcg null littermates were compared. Animal work was conducted under the approval of the University of Chicago and Northwestern IACUCs.

Immunofluorescence Microscopy for *Drosophila*, HEK Cells, and Mice.

Fifteen to 25 whole flies were anesthetized and covered in tissue freezing medium (TFM, Triangle Bioscience, Durham N.C.), chilled in isopentane for 5 minutes, followed by liquid nitrogen for another 5 minutes. Mouse muscles were harvested and snap-frozen in liquid nitrogen. The samples were kept frozen in −80° C. freezer until sectioning. Ten μm sections were cut from frozen tissues and immediately fixed in ice-cold methanol for 2 minutes and briefly rinsed in cold phosphate buffered saline (PBS) immediately afterwards. The sections were blocked in PBS containing 5% fetal bovine serum and 0.1% Triton-X for 2 hours at 4° C. The samples were then incubated with primary antibodies diluted in blocking solution at 4° C. overnight, followed by three 10-minute washes with PBS containing 0.1% Triton-X at 4° C. The sections were incubated with secondary antibody for 2 hours at 4° C. Samples were washed and then mounted with VECTASHIELD Mounting Medium with DAPI H-1200 (Vector Labs, Youngstown, Ohio). For HEK 293T cells, a sterilized cover slip was place in each well of 6-well cell culture plates before cells were plated. Transfection was performed on the next day and cells were harvested 40 hours after transfection. Cell culture media was aspirated and cells were rinsed once with cold PBS. Fixation and staining methods were the same as above. Images were collected using an Axiophot microscope with iVision software and edited using Adobe Photoshop CS4 and Image J in concert with NIH policy on appropriate image manipulation.

Antibodies.

Murine γ-sarcoglycan (SGCG) protein was detected with a rabbit polyclonal anti-antibody [McNally et al., Am J Hum Genet 59: 1040-1047 (1996)]. To detect Mini-Gamma protein, a rabbit polyclonal antibody was raised to the Xpress epitope (Pocono Rabbit Farms, Canadensis, Pa.) and affinity-purified. The rabbit polyclonal anti-SGCG antibody NBP1-90298 was used (Novus Biologicals, Littleton, Colo.). β-Sarcoglycan was detected with NCL-b-SARC (Leica Biosystems, Nussloch, Germany) and δ-sarcoglycan was detected with a polyclonal antibody [Hack et al., J Cell Sci 113 (Pt 14): 2535-2544 (2000)]. Secondary antibodies were Alexa Fluor® 488 Goat Anti-Rabbit and Alexa Fluor® 594 Goat Anti-Rabbit 594 (Invitrogen, Carlsbad, Calif.).

For microscopy, primary antibodies were used at 1:500 dilutions, and the secondary antibodies were used at 1:8000 with blocking buffer. For immunoblotting, antibodies were used at 1:1000 dilutions. For immune-precipitation (IP), 25 μL NCL-b-SARC or 10 μL rabbit anti-Xpress antibody was used from muscle lysates. Fifteen μL NCL-b-SARC or 5 μL rabbit anti-Xpress was used for IP from HEK cell lysates. Secondary antibodies were anti-mouse or anti-rabbit Horseradish Peroxidase conjugated antibodies (Jackson ImmunoResearch Laboratories, West Grove, Pa.) and used at 1:8000 dilution. Membranes were developed using Clarity Western ECL Substrate (Bio-Rad, Hercules, Calif.) and visualized by BioSpectrum Imaging System (UVP, Upland, Calif.).

Microsome Preparation.

Membrane-bound proteins were isolated following the protocol of Ohlendieck et al. [J Cell Biol 115: 1685-1694 (1991)] with modifications. Seven distinct muscle groups were dissected, including triceps, diaphragm, abdominal muscle, quadriceps, gluteus, hamstring and gastrocnemius muscles and combined. Muscles from one animal were homogenized in 12 mL pre-chilled Buffer A (20 mM sodium pyrophosphate, 20 mM sodium phosphate monohydrate, 1 mM $MgCl_2$, 0.303M sucrose, 0.5 mM EDTA, 1 mM PMSF, Roche COMPLETE protease inhibitor tablet) using a Tissue Tearor Homogenizer (Model 985-370 Type 2 with 7 mm probe, Biospec products, Bartlesville, Okla.). Homogenized tissues were then transferred to a 15 mL Dounce tissue grinder (Sigma-Aldrich) and were dounced 40 times using a tightness "B" pestle on ice. One hundred microliters of lysate was removed as "total protein" (T). Lysates were centrifuged at 9000 rpm for 18 minutes at 4° C. using SW41T1 rotor (13,900 g). The pellet was discarded and 100 μL supernatant was removed as "cytoplasmic protein" (C). The remainder of the supernatant was transferred to a new tube and centrifuged again at 13.200 rpm for 30 minutes at 4° C. (30,000 g). One hundred p L supernatant was removed as "light microsomes" (L). The pellet was resuspended in 12 mL pre-chilled KCL wash buffer (0.6M KCl, 0.303M sucrose, 50 mM Tris-HCl pH 7.4, 1 mM PMSF, Roche COMPLETE protease inhibitor tablet), incubated for 30 minutes on ice to remove actomyosin contamination. The suspension was then centrifuged again at 28,800 rpm for 30 minutes at 4° C. (142,000 g). The pellet was resuspended in 300 to 500 μL co-IP buffer (50 mM Tris-HCl, 150 mM NaCl, 1 mM EDTA, 1 mM EGTA, 0.1% Triton x-100, 0.1% SDS, 1 mM PMSF, Roche COMPLETE protease inhibitor tablet) and saved as "heavy microsomes" (H). For co-IP experiments, fresh heavy microsomes were used without freeze-thaw cycles. Protein concentration was determined using the BioRad assay.

Transfection of HEK Cells.

Human Embryonic Kidney (HEK 293T) cells were cultured in Dulbecco's Modified Eagle Medium (DMEM), to which 10% fetal bovine serum and 1% penicillin-streptomycin was added. FuGene® HD transfection reagent (Promega, Fitchburg, Wis.) was used to transfect HEK cells with sarcoglycan plasmids using the manufacturer's protocol. Cells were harvest 40-48 hours post transfection, briefly washed with ice-cold PBS once before 300 µL pre-chilled co-IP buffer per 10 cm plate was applied. Cells were collected and transferred to 1.5 mL centrifuge tubes on ice, titurated three times with insulin syringes. The lysates were then centrifuged at 14K rpm for 10 minutes at 4° C. and the supernatant was used for co-IP experiments.

Co-Immunoprecipitation from HEK Cells and Muscle.

Co-immunoprecipitation (co-IP) was performed according to published protocols [Hack et al., J Cell Sci 113 (Pt 14): 2535-2544 (2000)] with modifications. Five hundred micrograms of mouse skeletal muscle heavy microsomes or 650 µg HEK 293T cell lysates were pre-cleared with 45 µL Protein G Plus/Protein A Agarose Suspension (EMD Millipore Chemicals, Billerica, Mass.) for 1 hour at 4° C. The protein G/A beads were washed 3 times with co-IP buffer and then pre-cleared with a brief centrifugation. Pre-cleared samples were then incubated with antibodies at 4° C. for 3 hours or overnight. After primary incubation, the samples were incubated with protein G/A beads for 2 hours at 4° C. (100 µL bead suspension for heavy microsomes, 60 µL for HEK cell lysates). The samples were then centrifuged at 4000 rpm for 10 minutes at 4° C., and the supernatant was discarded. The beads were then washed for 7 times using pre-chilled wash buffer (co-IP buffer minus SDS). Equal amounts of 2× Laemmli SDS buffer was added to the beads and boiled at 95° C. for 5 minutes. The beads were then centrifuged at 14000 rpm for 2 minutes at room temperature and discarded, and the supernatant was used for IP.

Immunoblotting.

Protein samples were denatured, resolved on pre-cast 14% tris-glycine protein gels (Novex, San Diego, Calif.) and transferred to Immobilon-P membranes (Millipore, Bedford, Calif.). Reversible protein stain (Thermo Scientific, Waltham, Mass.) was performed on the membranes to evaluate transfer efficiency and equal protein loading. Membranes were blocked for 1 hour at room temperature with Starting Block T20 blocking buffer (Thermo Scientific, Waltham, Mass.), followed by incubation with primary antibody diluted in T20 blocking buffer for either 1 h at room temperature or overnight at 4° C. After primary incubation, the membranes were washed 3 times, 10 minutes each at room temperature with TBS containing 0.1% Tween-20. The membranes were then incubated with secondary antibody diluted in T20 blocking buffer for 1 hour at room temperature, followed by 3 washes.

Histology.

A cross-sectional strip of diaphragm muscle was obtained from midline of the muscle in a longitudinal axis. The strip was then fixed in formalin, dehydrated and embedded in paraffin. Seven µm sections were obtained and stained with hematoxylin and eosin (H&E). For central nucleated fiber analysis, three random fields each were obtained at 20× magnification from six animals of each genotype. For diaphragm thickness calculations, 3 evenly spaced fields along the length of the strip each were taken at 10× magnification from six animals of each genotype. The ruler tool in Photoshop (Adobe, San Jose, Calif.) was used to calculate the thickness of each field. Diaphragm thickness of each animal was the average of the three different fields.

Lentiviral Constructs and Transduction.

A packaged hTert lentivirus, which included a puromycin selection cassette, was purchased from Applied Biological Materials (ABM, Richmond, BC). A tamoxifen-inducible MyoD lentiviral construct (iMyoD), previously described, was kindly provided by Dr. Jeffrey Chamberlain (University of Washington) and packaged by the Northwestern Skin Disease Research Core [Kimura et al., Hum Mol Genet 17: 2507-2517 (2008)]. Human cells with a deletion of SGCG exon 6 (ex6del) and control cells were co-transduced with lentiviral hTert (MOI 5) and iMyoD (MOI 50), then subjected to puromycin selection (10 days (d), 1 µg/mL; InvivoGen, San Diego, Calif.). Lentiviral transductions were performed in growth media without Pen/Strep in the presence of polybrene (8 µg/mL) (Millipore, Billerica, Mass.).

Hydroxyproline (HOP) Assay and Echocardiography.

Hydroxyproline content was determined as previously described [Heydemann et al., Neuromuscul Disord 15: 601-609 (2005)]. Echocardiography was performed as previously described [Goldstein et al., Hum Mol Genet 23: 6722-6731 (2014)].

In Vitro Human Cell Culture and AON Transfection.

Primary fibroblasts were derived from a skin biopsy obtained from LGMD2C patients. Primary fibroblasts from a healthy control subject (CRL-2565) were obtained from the American Type Culture Collection (ATCC, Manassas, Va.). Written and informed consent was obtained in accordance with the University of Chicago's Institutional Review Board. All work was conducted under the University of Chicago and Northwestern's Institutional Review Boards. LGMD 2C (ex6del), LGMD 2C (ex7del) and control cells were transduced with an inducible MyoD lentiviral construct (iMyoD), previously described [Kimura et al., Hum Mol Genet 17, 2507-2517 (2008); Kendall et al., Science Translational Medicine 4: 164ra160 (2012)]. After 4OH-tamoxifen induction and culture in differentiation media (5 µM/48 h; 10-12d diff), fibroblasts were reprogrammed to express myogenic markers, including the SGCG transcript, and formed multinucleated myotubes. Exon skipping with AONs utilized 2'-O-methyl phosphorothioate (2OMePS) AONs designed in accordance with previously described guidelines, and synthesized by Integrated DNA Technologies (IDT, Coralville, Iowa) [Aartsma-Rus, Methods in molecular biology 867: 117-129 (2012)]. PMOs were synthesized by GeneTools (Philomath, Oreg.). Sequences are defined in Table 2, below. 2OmePS were transfected into cells on differentiation day 9 (6 h, 100 nM per AON) in serum free media at a ratio of 2 µL:1 µg DNA. PMOs were covalently linked to an octa-guanidine dendrimer vivo-moiety for cell delivery [Morcos et al, Biotechniques 45: 613-4 (2008)]. Cells were isolated for transcript analysis 48-72 hours after AON treatment. On day 12, total RNA was isolated from cells, reverse transcribed, and evaluated for full-length and internally truncated SGCG expression via PCR and gel electrophoresis.

TABLE 2

Antisense Oligonucleotide (AON) Sequences contemplated for exon skipping.

| huSGCG Exon (chemistry/ SEQ ID NO) | Sequence (5'-3') | | |
|---|---|---|---|
| Exon 4* (SEQ ID NO: 3) | attttgcaaattttataaatctctttctagGACTCATCTCTGCTTCTACAATCAA CCCAGAATGTGACT[1]GTAAATGCGCGCAACTCAGAAGGGGAGGTCACAGG[2]CAGGT TAAAAGTCGgtgagtccagcttcatcatggtgc[3]tttgca | | |
| +15+39 E42OMe** (SEQ ID NO: 4) | AGUCACAUUCUGGGUUGAUUGUAGA | 25nt | target = [1] |
| +15+39 E4PMO (SEQ ID NO: 5) | AGTCACATTCTGGGTTGATTGTAGA | 25nt | target = [1] |
| +50+74 E42OMe (SEQ ID NO: 6) | CCUGUGACCUCCCCUUCUGAGUUGC | 25nt | target = [2] |
| +50+74 E4PMO (SEQ ID NO: 7) | CCTGTGACCTCCCCTTCTGAGTTGC | 25nt | target = [2] |
| +88+112 E42OMe (SEQ ID NO: 8) | GCACCAUGAUGAAGCUGGACUCACC | 25nt | target = [3] |
| +88+112 E4PMO (SEQ ID NO: 9) | GCACCATGATGAAGCTGGACTCACC | 25nt | target = [3] |
| Exon 5 (SEQ ID NO: 10) | gtttataataaactgttttaattcttcagGTCCCAAAATGGTAGAAGTCCAGAAT CAACAGTTTCAG[1]ATCAACTCCAACGACGGCAAGCCACTATTTACTGTAGATGAG AAGGAAGTTGTGGTTGGTACAGATAAACTTCGAGTAACTGgtatgtactaactcg agaaaaacacaacat | | |
| +14+38 E52OMe (SEQ ID NO: 11) | CUGAAACUGUUGAUUCUGGACUUCU | 25nt | target = [1] |
| +14+38 E5PMO (SEQ ID NO: 12) | CTGAAACTGTTGATTCTGGACTTCT | 25nt | target = [1] |
| Exon 6 (SEQ ID NO: 13) | tcctgatacatctttgttttttgtttagGGCCTGAAGGGGCT[1,2]CTTTTTGAACA T[3]TCAGTGGAG[4]ACACCC[5]CTTGTCAGAGCCGACCCGTTTCAAGAC6CTTAGgtaa gaattttgttcaaatattaacaacc | | |
| -15+14 E62OMe (SEQ ID NO: 14) | AGCCCCUUCAGGCCCUAAACAAAAAACAA | 29nt | target = [1] |
| -15+14 E6PMO (SEQ ID NO: 15) | AGCCCCTTCAGGCCCTAAACAAAAAACAA | 29nt | target = [1] |
| -10+14 E62OMe (SEQ ID NO: 16) | AGCCCCUUCAGGCCCUAAACAAAAA | 25nt | target = [2] |
| -10+14 E6PMO (SEQ ID NO: 17) | AGCCCCTTCAGGCCCTAAACAAAAA | 25nt | target = [2] |
| +2+26 E62OMe (SEQ ID NO: 18) | AUGUUCAAAAGAGCCCCUUCAGGC | 25nt | target = [3] |
| +2+26 E6PMO (SEQ ID NO: 19) | ATGTTCAAAAGAGCCCCTTCAGGC | 25nt | target = [3] |
| +1+27 E62OMe dT (SEQ ID NO: 20) | AAUGUUCAAAAGAGCCCCUUCAGGCC | 26nt | dT target |
| +1+27 E6PMO dT (SEQ ID NO: 21) | AATGTTCAAAAGAGCCCCTTCAGGCC | 26nt | dT target |
| +11+35 E62OMe (SEQ ID NO: 22) | CUCCACUGAAUGUUCAAAAGAGCC | 25nt | target = [4] |
| +11+35 E6PMO (SEQ ID NO: 23) | CTCCACTGAATGTTCAAAAGAGCC | 25nt | target = [4] |
| +10+36 E62OMe dT (SEQ ID NO: 24) | UCUCCACUGAAUGUUCAAAAGAGCCC | 26nt | dT target |
| +10+36 E6PMO dT (SEQ ID NO: 25) | TCTCCACTGAATGTTCAAAAGAGCCC | 26nt | dT target |
| +17+40 E62OMe (SEQ ID NO: 26) | GGGUGUCUCCACUGAAUGUUCAAA | 24nt | target = [5] |
| +17+40 E6PMO (SEQ ID NO: 27) | GGGTGTCTCCACTGAATGTTCAAA | 24nt | target = [5] |
| +43+68 E62OMe (SEQ ID NO: 28) | GUCUUGAAACGGGUCGGCUCUGACA | 25nt | target = [6] |
| +43+68 E6PMO (SEQ ID NO: 29) | GTCTTGAAACGGGTCGGCTCTGACA | 25nt | target = [6] |
| Exon 7 (SEQ ID NO: 30) | ttttttttgtgcttcttttcctcatctcagATTAGAATCCCCCACTCGGAGTCTA AGCATGGATGCC[1]CCAAGGGGTGTGCATATTCAAGCTCACGCTGGGAAAATTGAG GCGCTTTCTCAAATGGATATTCTTTTTTCATAGTAGTGATGGAATGgtgag[2]ttca ttcacagatcagcctcctact | | |

TABLE 2-continued

Antisense Oligonucleotide (AON) Sequences contemplated for exon skipping.

| huSGCG Exon (chemistry/ SEQ ID NO) | Sequence (5'-3') | | |
|---|---|---|---|
| +13+37 E72OMe (SEQ ID NO: 31) | GGCAUCCAUGCUUAGACUCCGAGUG | 25nt | target = 1 |
| +13+37 E7PMO (SEQ ID NO: 32) | GGCATCCATGCTTAGACTCCGAGTG | 25nt | target = 1 |
| +105+129 E72OMe (SEQ ID NO: 33) | CUCACCAUUCCAUCACUACUAUGAA | 25nt | target = 2 |
| +105+129 E7PMO (SEQ ID NO: 34) | CTCACCATTCCATCACTACTATGAA | 25nt | target = 2 |

*human SGCG coding regions (upper case), with flanking intronic regions (lower case).
**Nomenclature indicates AON target site. The number of nt (-/+) from start of the indicated SGCG exon = +1. This is followed by the AON chemistry used 2'-O-methyphosphorothioate (2OMe) or Phosphorodiamidate morpholino (PMO). For exon 6, the 521ΔT mutation is identical to that depicted except for the loss of a single "T" two bases to the right of the superscript "2" shown above in SEQ ID NO: 13, and AONs to this region are depicted with "dT" nomenclature.

Myogenic Reprogramming of Fibroblasts.

To induce myogenic reprogramming, fibroblasts were seeded on culture plates (ThermoFisher, Waltham, Mass.) or glass coverslips (#1.5, Electron Microscopy Sciences, Hatfield, Pa.) in growth media (30,000 cell/cm2). When cells reached confluence, 5 µM 4OH-tamoxifen (Sigma, St. Louis, Mo.) was added to growth media without Pen/Strep. After 48 hours, differentiation media (1:1 DMEM:Ham's F10; 5% FBS; 2% Normal Horse Serum (NHS); 1% insulin-transferrin-selenium (Sigma)) was added to cells with 1 µM tamoxifen. After 4 days, differentiation media was replaced, without 4OH-tamoxifen. Cells were assessed for markers of myogenic differentiation from after 10-12 days in differentiation media.

Antisense Oligonucleotide Design and Transfection.

2'-O-methyl phosphorothioate (2OmePS) anti-sense oligonucleotides (AON) were designed in accordance with previously described guidelines [Aartsma-Rus et al., Methods in molecular biology 867: 117-129 (2012)]. AON were synthesized by Integrated DNA Technologies, IDT (Table 2). Dose response was evaluated for single 2OMePS AON targeting SGCG exons 4, 5, or 7 at concentrations from 100-500 nM. On differentiation day 9, AONs were transfected into ex6del cells in serum free media using Lipofectamine 3000 (Life Technologies, Grand Island, N.Y.) at a ratio of 2 µL:1 µg DNA. After 6 hours, media was replaced with differentiation media without 4OH-tamoxifen, and cells were isolated for analysis 48 hours later. For read frame correction of the SGCG mutation, AONs targeting exons 4, 5, and 7 were co-transfected on differentiation day 9 as described (100 nM of each AON, 300 nM total). After 6 hours, media was replaced with differentiation media without 4OH-tamoxifen. Cells were isolated for analysis 3 days after AON transfection.

RNA Isolation, RT-PCR, and qPCR.

Total RNA was isolated with TRIzol (Life Technologies, Grand Island, N.Y.) and reverse-transcribed using qScript cDNA Supermix (Quanta Biosciences, Gaithersburg, Md.). For detection of human SGCG transcripts, Taqman based PCR was used to amplify 50-100 ng cDNA with the following primer set ex1/2Fwd 5'-TCTAAGATGGTGCGT-GAGCAG-3' (SEQ ID NO: 35) and ex8R 5'-GCCACA-GACAGGTACAGCTr-3' (SEQ ID NO: 36). PCR products were separated on a 1.5% 1XTBE low-melt agarose gel (NuSeive, Lonza, Walkersville, Md.) supplemented with 10 µg/mL ethidium bromide (Sigma, St. Louis, Mo.), and analyzed with the UVP Transluminator (BioSpectrum, Upland, Calif.).

Immunofluorescence Microscopy for LGMD2C Cells.

For detection of MyoD and desmin, cells plated on glass coverslips were washed 3 times with PBS, fixed with 4% paraformaldehyde (15 minutes (min), RT), rinsed with PBS, permeabilized in 0.25% Triton-X in PBS (20 min, RT), and blocked with 10% NHS in PBS (1 h, 4° C.). Coverslips were incubated overnight at 4° C. with primary antibodies diluted with blocking buffer (PBS supplemented with 0.1% Triton-X and 2% NHS). Cells were washed 3 times in PBS, incubated with secondary antibodies diluted in blocking buffer (1 hour, RT), rinsed with PBS, incubated with Hoechst 3342 diluted 1:10000 in PBS (15 min, RT), washed 3 times with PBS, and mounted with VECTASHIELD Mounting Medium H-1000 (Vector Labs, Youngstown, Ohio). To evaluate MyoD expression, cells were cultured on coverslips for 48 hours and treated with 4OH-tamoxifen (5 µM, 24 hours). Desmin expression was evaluated in reprogrammed cells cultured on coverslips (+/−4OH-tamoxifen, 10-12d diff). The anti-MyoD rabbit polyclonal C-20 (1:2000; Santa Cruz Biotechnology, Dallas, Tex.) and mouse monoclonal anti-desmin D1033 (1:1000, Sigma) were used to detect MyoD and desmin respectively, with secondary antibodies Alexa Fluor® 594 donkey anti-rabbit and Alexa Fluor® 594 donkey anti-mouse (Life Technologies, Grand Island, N.Y.).

Example 1

Expression of Murine Mini-Gamma Rescues a *Drosophila* Model of Muscular Dystrophy γ-sarcoglycan is type II transmembrane protein with a short intracellular domain, a single transmembrane pass and a larger carboxy-terminal extracellular domain. An internally truncated γ-sarcoglycan was generated, and this truncation, referred to as Mini-Gamma, reflects the deletion of the protein regions encoded by exons 4, 5, 6 and 7 (FIG. 1A). To test the functionality of Mini-Gamma, the GAL4/UAS system was used to express murine Mini-Gamma in a previously established *Drosophila* model of muscular dystrophy [Brand et al., Development 118: 401-415 (1993); Allikian et al., Hum Mol Genet 16: 2933-2943 (2007)]. *Drosophila* has a single ortholog that is equally related to mammalian γ- and δ-sarcoglycan (35% identical, 56% similar to each). Sgcd840 flies are deleted for the *Drosophila* Sgcd gene and develop impaired motility and dilated heart tubes in adult flies [Allikian et al., Hum Mol Genet 16: 2933-2943 (2007)]. The sarcoglycan complex is localized at the muscle membrane, and loss of function mutations in mice and humans result in absence of plasma membrane-associated staining [Vainzof et al., Hum Mol Genet 5: 1963-1969 (1996); Mizuno et al., Biochem Biophys Res Commun 203: 979-983 (1994); Hack et al., J Cell Sci 113 (Pt 14): 2535-2544 (2000); Durbeej et al., Mol Cell 5: 141-151 (2000); Duclos et al., J Cell Biol 142: 1461-1471 (1998)]. Full-length murine γ-sarcoglycan (mGSG) localized to the sarcolemma when expressed in Sgcd840 muscle (FIG. 1B, upper left), indicating that the murine γ-sarcoglycan normally translocates in *Drosophila* muscle. Expression of murine Mini-Gamma showed the same distinct plasma membrane localization when expressed in Sgcd840 flies (FIG. 1B, upper right). Expression of Mini-Gamma in Sgcd840 hearts also showed plasma membrane-associated staining in the thin-walled heart tube structure (FIG. 1B, lower panel). Expression of Mini-Gamma in wildtype flies showed less distinct membrane localization and this decrement in Mini-Gamma membrane staining is consistent with competition between Mini-Gamma and the endogenous fly Sgcd-encoded protein.

Figure 8:
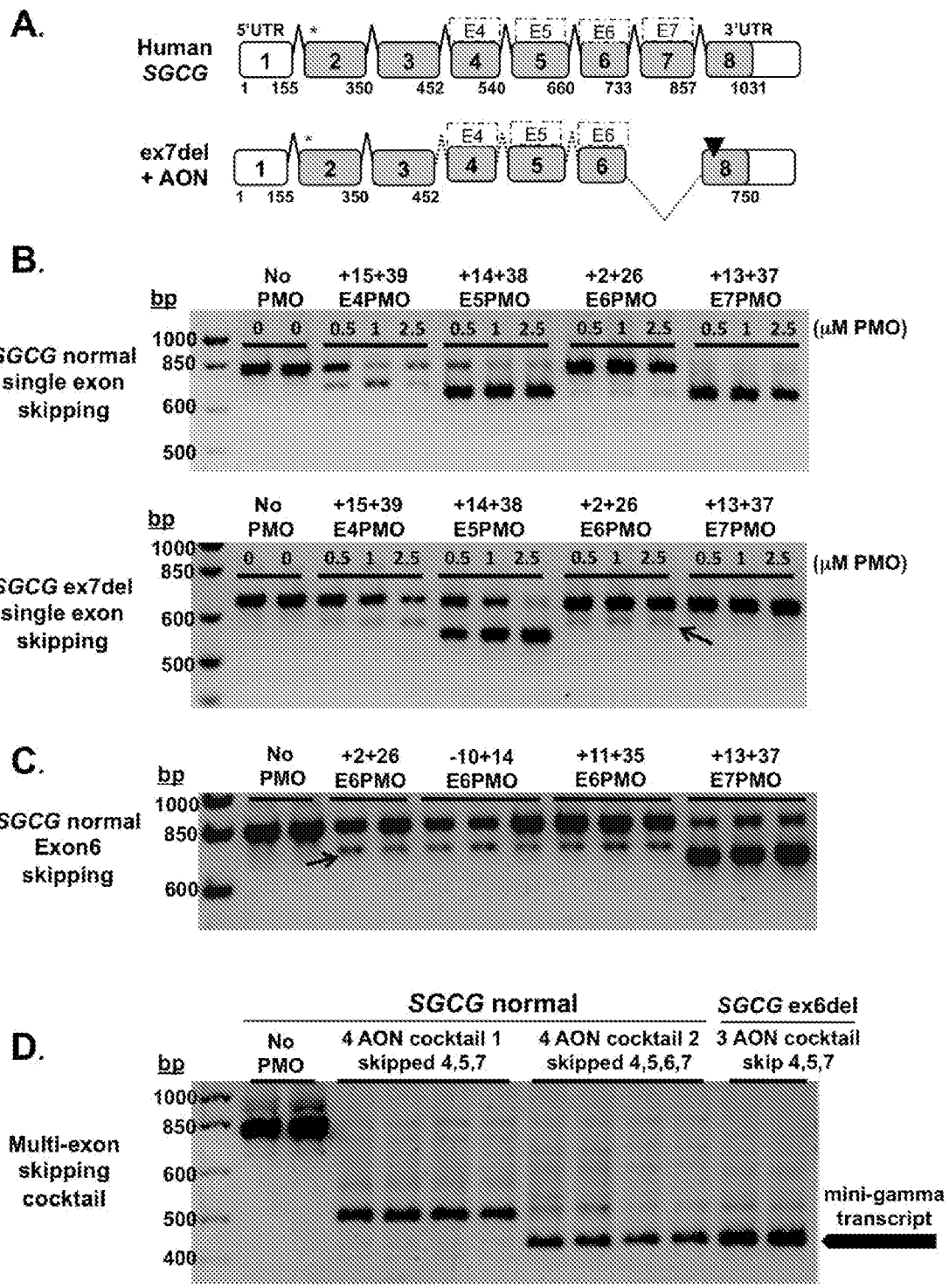
FIG. 8 depicts results of exon skipping using PMO chemistry. Results are shown using reprogrammed fibroblasts from SGCG normal, SGCG ex6 del, and an LGMD 2C patient who has homozygous deletion for exon 7 (ex7del). A. The exon organization for SGCG normal control and SGCG ex7del LGMD 2C patient who lacks exon 7 on both alleles as the cause of LGMD 2C. Numbers indicate the nucleotide number starting at exon 1. The asterisk indicates the start site for protein translation and the triangle indicates the premature stop codon in ex7del SGCG mRNA. B. Gel electrophoresis of RT-PCR amplified SGCG normal (top) and ex7del (bottom) SGCG transcripts, after treatment with single PMO AONs targeting exons 4, 5, 6, or 7 (0.5-2.5 µM/AON, 48 hours). Black arrow on ex7del gel indicates the expected band generated from successful skipping of exon 6 (using SEQ ID NOs: 5, 12, 19, and 32). C. Gel electrophoresis of RT-PCR amplified control SGCG transcripts treated with high dose PMOs (SEQ ID NOs: 19, 17, and 23, respectively) (4 µM, 48 hours (h)) against 3 different exon 6 targets, demonstrating the ability for single exon skipping of exon 6 in control cells. Far right: exon 7 skipping reference with low dose E7PMO (SEQ ID NO: 32) (0.5 µM, 48 hours). Multiple replicates for each treatment are shown. D. Multi-exon skipping of the SGCG transcript mediated by combinatorial AON treatment (48 hours). Cocktail 1 includes SEQ ID NOs: 5, 12, 19 and 32; Cocktail 2 includes SEQ ID NOs: 5, 12, 23, and 32; the 3 AON Cocktail includes SEQ ID NOs: 5, 12, and 32. Cocktails containing PMOs directed against exons 4, 5, and 7 used 1 µM, 1 µM, 0.5 µM, respectively. The read frame corrected internally truncated Mini-Gamma skipped product was generated in control cells treated with cocktail 2 (black arrow). The far right lanes show the generation of the Mini-Gamma SGCG transcript in LGMD 2C patient cells with an exon 6 deletion (ex6del).
Figure 9:
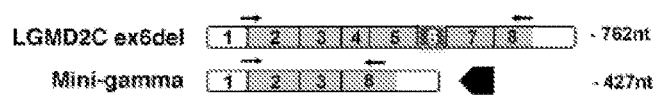
FIG. 9 depicts multi-exon skipping in Limb Girdle Muscular Dystrophy type 2C. A. MyoD-reprogrammed fibroblasts were induced into muscle cell differentiation and then treated with 2'O methyl (2OMe) antisense oligonucleotides (AONs). AONs targeting exons 4, 5, and 7 (100 nM/AON, 300 nM total). RT-PCR demonstrated the expected skipped products, including the smallest product representing exons 2, 3 and 8 and deleted for exons 4, 5, and 7 (arrow). Results from 4 independent replicates are shown for AON treatment. B. The upper panel shows a chromatogram of the sequencing results documenting the expected splice product created by AON-induced exon skipping. A read-frame corrected mini-gamma transcript is shown that includes exons 2, 3 and 8. The bottom panel shows the control chromatogram depicting the normal splice junction of exons 3 linked to exon 4. The black box in the upper panel indicates a synonymous variant observed in exon 8 of this LGMD 2C patient. SEQ ID NOs: 4, 11, and 31 were used in these experiments.
Figure 9:
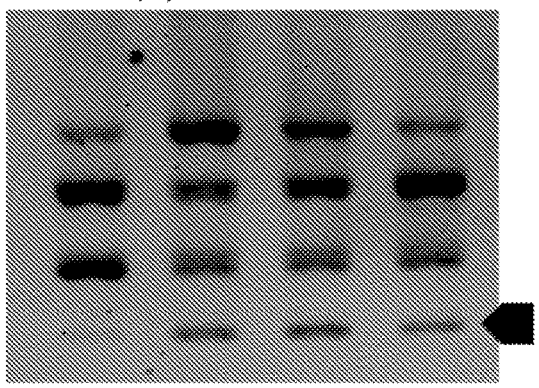
Figure 9:
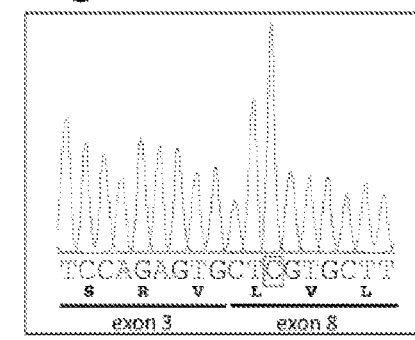
Figure 9:
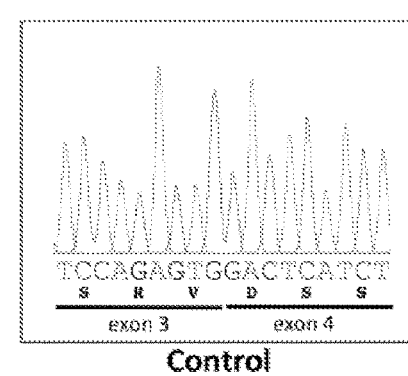
Figure 10:
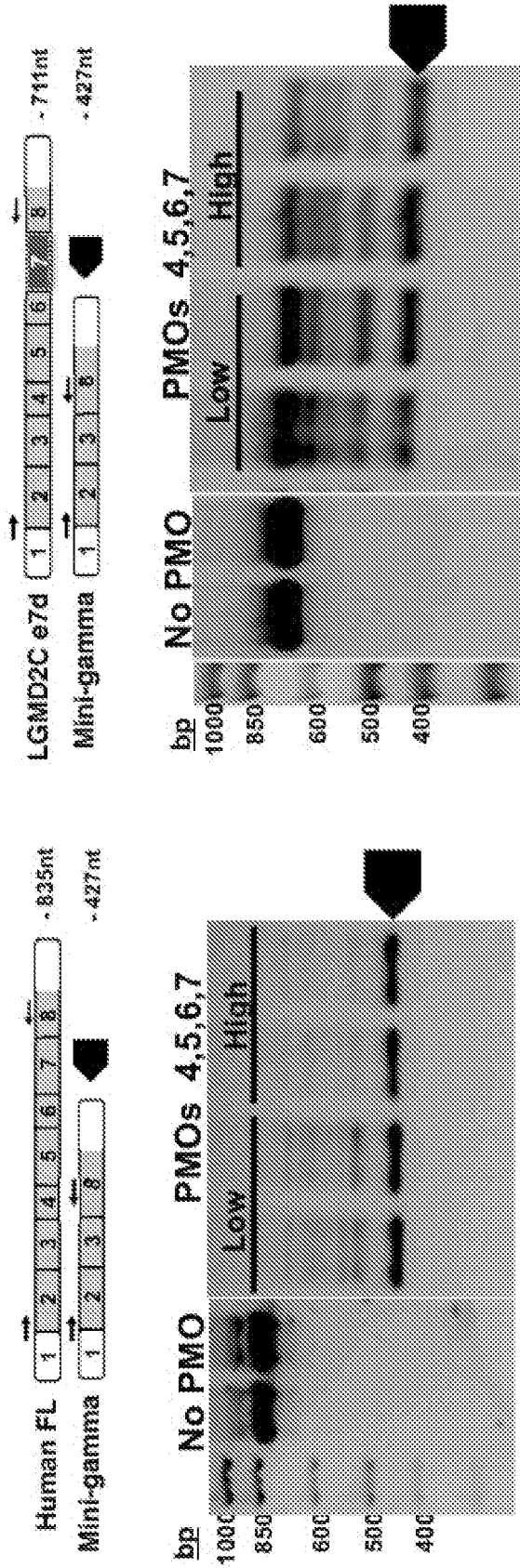
FIG. 10. Vivo-morpholino PMO AONs mediate efficient read frame correction in normal control human and SGCG mutant cells. Multi-exon PMO induced exon skipping generated the mini-gamma transcript in both control (A) and mutant cell lines (B). Gel electrophoresis of RT-PCR products demonstrated a band approximately 425 nt, representative of exons 2, 3 and 8 inclusion and exons 4, 5, 6, and 7 deletion (black arrow). Intermediate products were also observed in the LGMD 2C patient shown in B. This individual lacks exon 7 of SGCG as the cause of LGMD 2C. For PMO 4,5,6,7 cocktail in A and B, Low dose equaled 1, 1, 1, 0.5 µM for PMO 4, 5, 6, and 7 respectively; High dose was 1, 1, 2, 0.5 µM of each PMO. SEQ ID NOs: 5, 12, 23, and 32 were used in these experiments.
Figure 11:
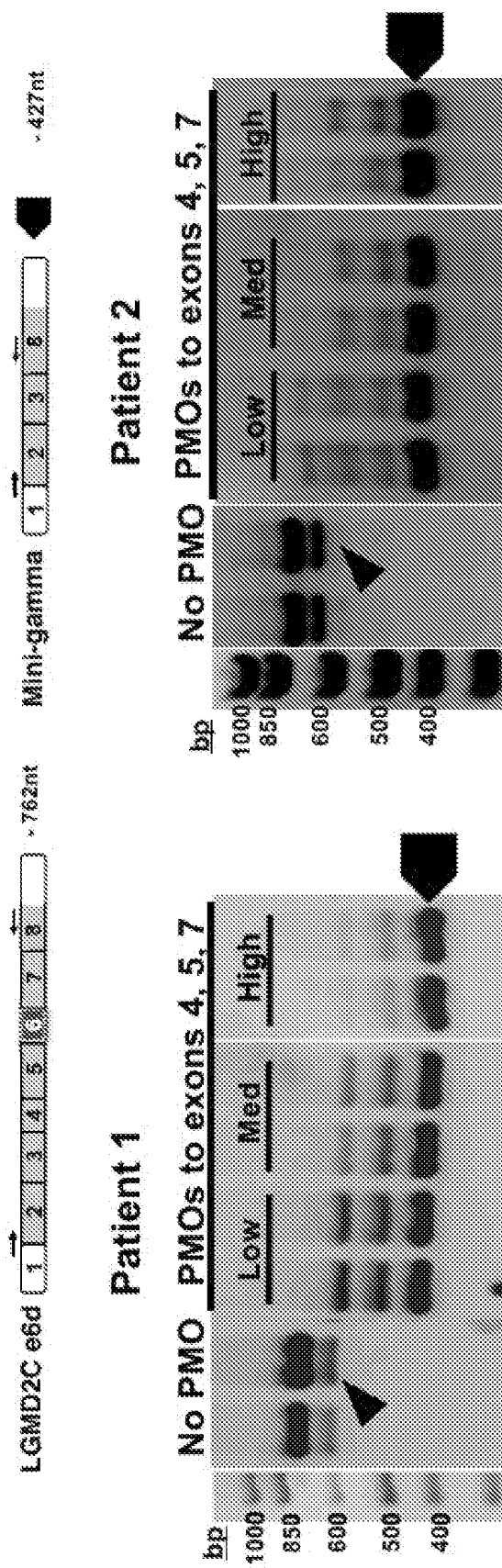
FIG. 11. Vivo-morpholino PMO AONs mediate efficient read frame correction in cells from two additional SGCG mutant LGMD 2C patients. The black arrowhead indicates endogenous exon 7 skipping is present in two different lines from individuals containing the same exon 6 deletion of SGCG. For PMO 4,5,7 cocktail in C, Low dose was 1, 1, 0.5 µM of each PMO; Medium was 1, 1, 1 µM; and High was 2, 2, 1 µM for PMO 4, 6, and 7, respectively. SEQ ID NOs: 5, 12, 23, and 32 were used in these experiments.

To measure *Drosophila* heart function, optical coherence tomography (OCT) was used to measure heart tube dimension during both contraction and relaxation [Wolf et al., Drug Discov Today Dis Models 5: 117-123 (2008)]. Sgcd840 flies had dilated heart tubes with significantly increased end systolic dimension (ESD) compared to wild type (FIG. 1C). Expression of Mini-Gamma in the heart tube was sufficient to restore ESD to wild type dimensions (FIG. 1C). A representative OCT tracing demonstrates the dilated nature in Sgcd840 flies and rescue of this phenotype by Mini-Gamma (MG) (FIG. 1C). Sgcd840 flies display locomotive defects as a result of skeletal muscle degeneration [Allikian et al., Hum Mol Genet 16: 2933-2943 (2007)]. A *Drosophila* activity monitor was used to record fly spontaneous activity over 24-48 hours (FIG. 8). Nocturnal activity was compared since insect behavior is consistent during this interval with less diurnal variation. Compared to wild type flies, Sgcd840 flies have reduced nocturnal activity (FIG. 1D). Expression of Mini-Gamma in Sgcd840 flies significantly improved the activity of Sgcd840 flies (FIG. 1D). Expression of Mini-Gamma did not fully restore activity of Sgcd840 flies. However, it is noted that expression of mGSG (murine full-length γ-sarcoglycan) resulted in similar level of rescue of activity as Mini-Gamma (FIG. 1D, lower right) suggesting that at least part of the failure to fully restore activity derives from the differences between *Drosophila* and mammalian sarcoglycans.

Example 2

Mini-Gamma Interacts with Other Sarcoglycans

Figure 2:
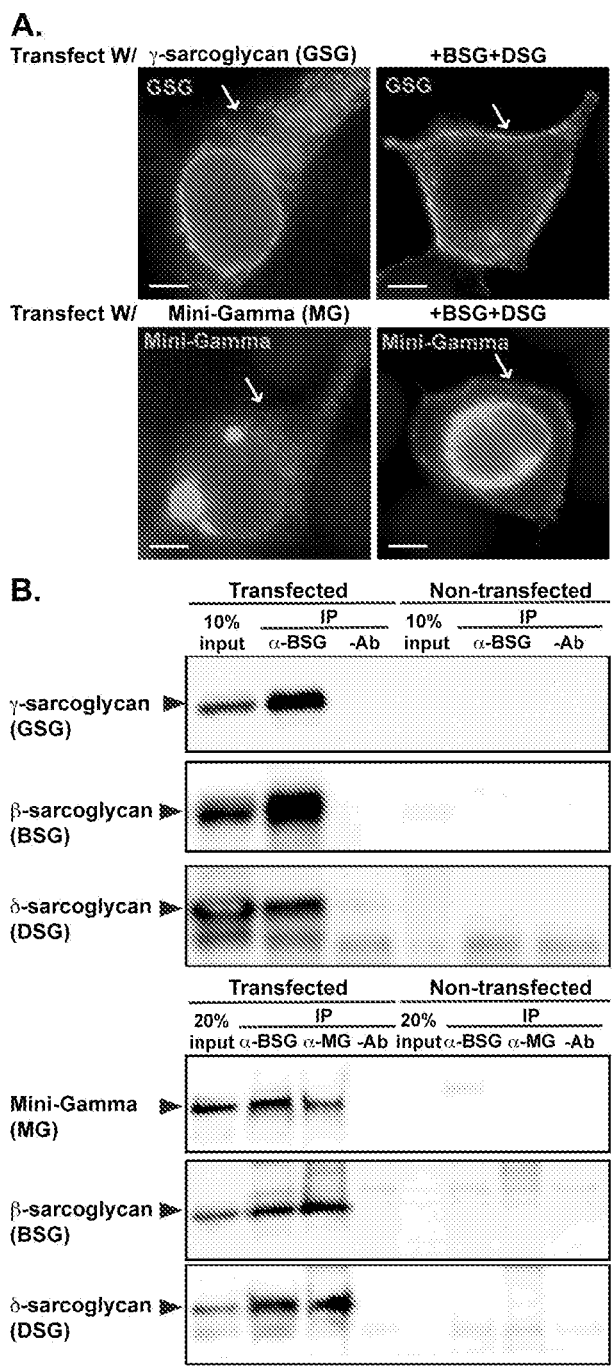
FIG. 2 shows that Mini-Gamma interacts with β and δ-sarcoglycan. Plasmids encoding mammalian sarcoglycans were expressed in HEK cells. A. When expressed alone, both Mini-Gamma and full-length γ-sarcoglycan (GSG) were not found at the plasma membrane and instead were retained in the cytoplasm and perinuclear regions, consistent with previous reports that association with the β/δ core is required for membrane targeting [Shi et al., Muscle Nerve 29: 409-419 (2004)] (arrows in left panels show little to no plasma membrane trafficking.) Co-expression of β-, δ and γ-sarcoglycans together resulted in plasma membrane enrichment of γ-sarcoglycan (GSG) (arrow in top right panel.) Similarly, expression of Mini-Gamma with β- and δ-sarcoglycan resulted in plasma membrane translocation of Mini-Gamma. Scale bar=5 μm. B. Co-immunoprecipitation was performed to examine sarcoglycan complex formation from HEK heterologous cell expression experiments. Immunoprecipitation with an anti-β-sarcoglycan antibody, a complex containing β-, δ and γ-sarcoglycan was detected in β/δ/γ co-expressing cells (upper panels). Likewise, immunoprecipitation with the same anti-β-sarcoglycan antibody demonstrated an interaction among β-, δ- and Mini-Gamma (lower panels). Immunoprecipitation for Mini-Gamma (MG) using an antibody against the Xpress tag also detected β- and δ-sarcoglycan.

Murine sarcoglycan proteins were transiently expressed in the human embryonic kidney (HEK 293T) cells to examine their intracellular localization. It was previously shown that β- and δ-sarcoglycan form a core subunit, followed by the addition of γ-sarcoglycan to the complex [Hack et al., J Cell Sci 113 (Pt 14): 2535-2544 (2000); Noguchi et al., Eur J Biochem 267: 640-648 (2000); Shi et al., Muscle Nerve 29: 409-419 (2004)]. Expression of the individual sarcoglycan subunits, β-, γ- or δ-sarcoglycan or Mini-Gamma (MG), produced accumulation of immunoreactivity in a perinuclear pattern and not the expected plasma membrane position (FIG. 2A), consistent with prior reports of interdependency for normal intracellular trafficking [Shi et al., Muscle Nerve 29: 409-419 (2004)]. Co-expression of β-, γ- and δ-sarcoglycan together resulted in plasma membrane enrichment of γ-sarcoglycan. Similarly, expression of β- and δ-sarcoglycan and Mini-Gamma also resulted in plasma membrane associated Mini-Gamma staining (FIG. 2A, lower panel right). Immunoprecipitation of expressed sarcoglycan subunits using an anti-β-sarcoglycan antibody confirmed that complexes containing β-, γ- and δ-sarcoglycan could be detected (FIG. 2B, top panels). Likewise, immunoprecipitation with anti-β-sarcoglycan demonstrated an interaction among β- and δ-sarcoglycan and MG (FIG. 2B, bottom panels). Immunoprecipitation for Mini-Gamma also detected β- and δ-sarcoglycan (FIG. 2B, bottom panels). These data demonstrate that Mini-Gamma formed a complex with β- and δ-sarcoglycan like full-length γ-sarcoglycan.

Example 3

Mini-Gamma is Incorporated into the Sarcoglycan Complex In Vivo

Figure 3:
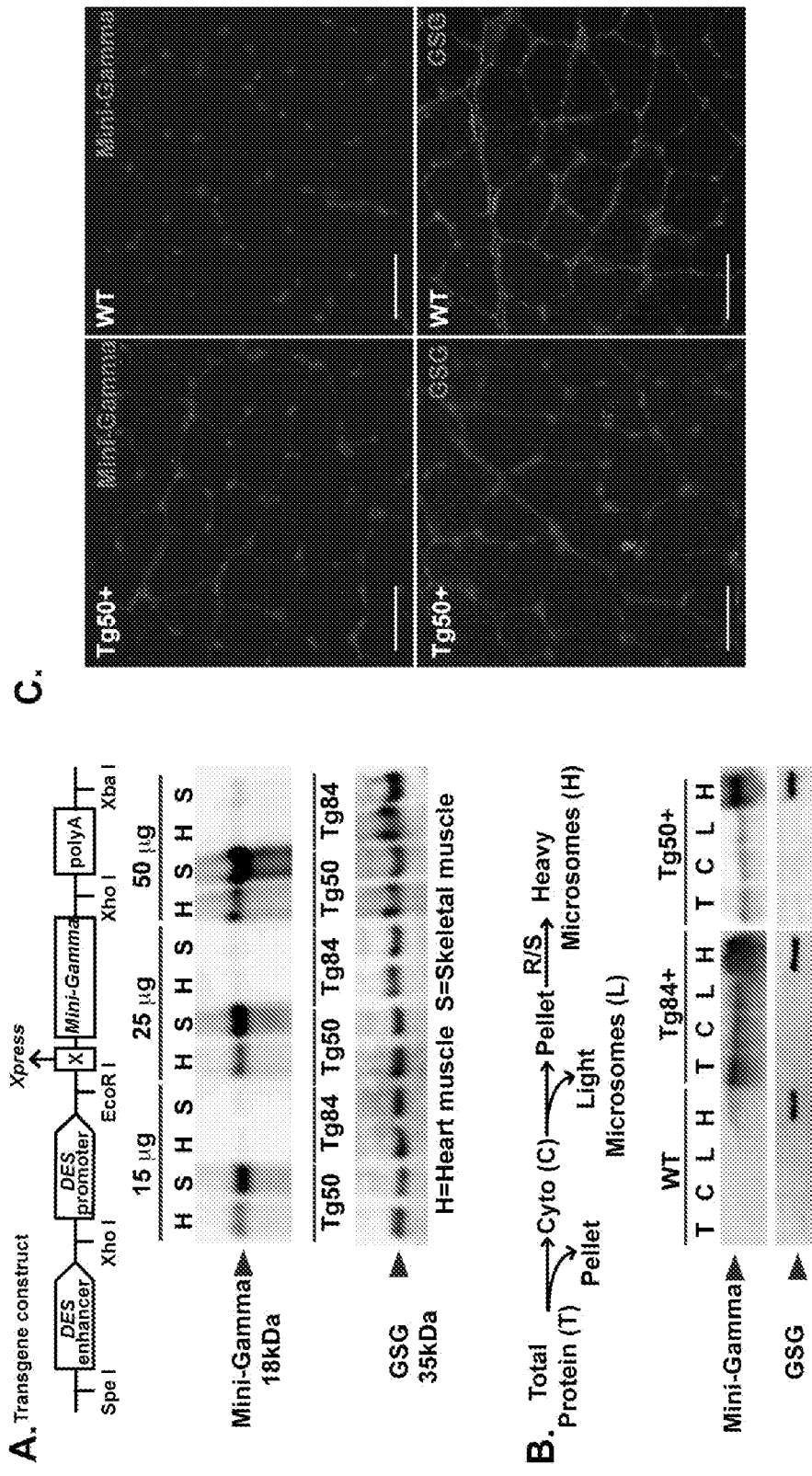
FIG. 3 shows that Mini-Gamma was incorporated into the sarcoglycan complex in vivo. A. Transgenic mice expressing murine Mini-Gamma under the control of the human desmin (DES) promoter were generated. B. Two independent lines of Mini-Gamma were characterized; Tg50 had high expression while Tg84 had lower level expression. C. To assess sarcoglycan complex formation, microsomal preparations were generated from transgenic mouse muscle. Membrane-associated microsomes were isolated. The sarcoglycan complex is known to enrich in the heavy microsomal fraction (H), which contains the secretory system and plasma membrane [Ohlendieck et al., J Cell Biol 115: 1685-1694 (1991)]. Similar to endogenous γ-sarcoglycan, Mini-Gamma was highly enriched in heavy microsomes isolated from both transgenic lines. D. Mini-Gamma was found at the plasma membrane of skeletal muscle, as seen in cross sections from Tg50+ mouse muscle. Endogenous γ-sarcoglycan was slightly diminished in Tg50+ animals compared to identically and simultaneously processed muscle sections from wildtype (WT), suggesting competition for plasma membrane localization between Mini-Gamma and endogenous γ-sarcoglycan. Scale bar=50 µm.

To test the function of Mini-Gamma in vivo, transgenic mice expressing Mini-Gamma under the control of the desmin promoter were generated. The desmin promoter is known to express in both heart and skeletal muscle [Pacak et al., Genet Vaccines Ther 6: 13 (2008)]. Two lines were characterized; Tg50 demonstrated high level expression while Tg84 had lower level expression, as detected by the epitope tag (FIG. 3A). Muscle microsomal fractionation was used to monitor the expression of Mini-Gamma in muscle by separating fractions of crude total muscle lysates (T) into cytoplasmic fraction (C), light microsomes (L) and heavy microsomes (H). Sarcolemmal, ER and Golgi-associated membrane proteins are enriched in the heavy microsomal fraction. In wild type animals, sarcoglycan proteins and other membrane-bound DGC components are mainly found in the muscle heavy microsome fraction [Ohlendieck et al., J Cell Biol 115: 1685-1694 (1991)]. Similar to the endogenous γ-sarcoglycan, Mini-Gamma protein was highly enriched in heavy microsomes from both transgenic lines (FIG. 3B). Indeed, Mini-Gamma protein demonstrated sarcolemmal-associated staining in cross sectional analysis of skeletal muscle (FIG. 3C, left panels). Interestingly, endogenous γ-sarcoglycan was slightly diminished in Mini-Gamma transgenic animals compared to identically and simultaneously processed muscle sections from wild type animals, suggesting competition for plasma membrane localization between Mini-Gamma and the endogenous γ-sarcoglycan (FIG. 3C, compare bottom two panels).

Example 4

Mini-Gamma Ameliorates Skeletal Muscle Defects in γ-Sarcoglycan Null Mice

Figure 4:
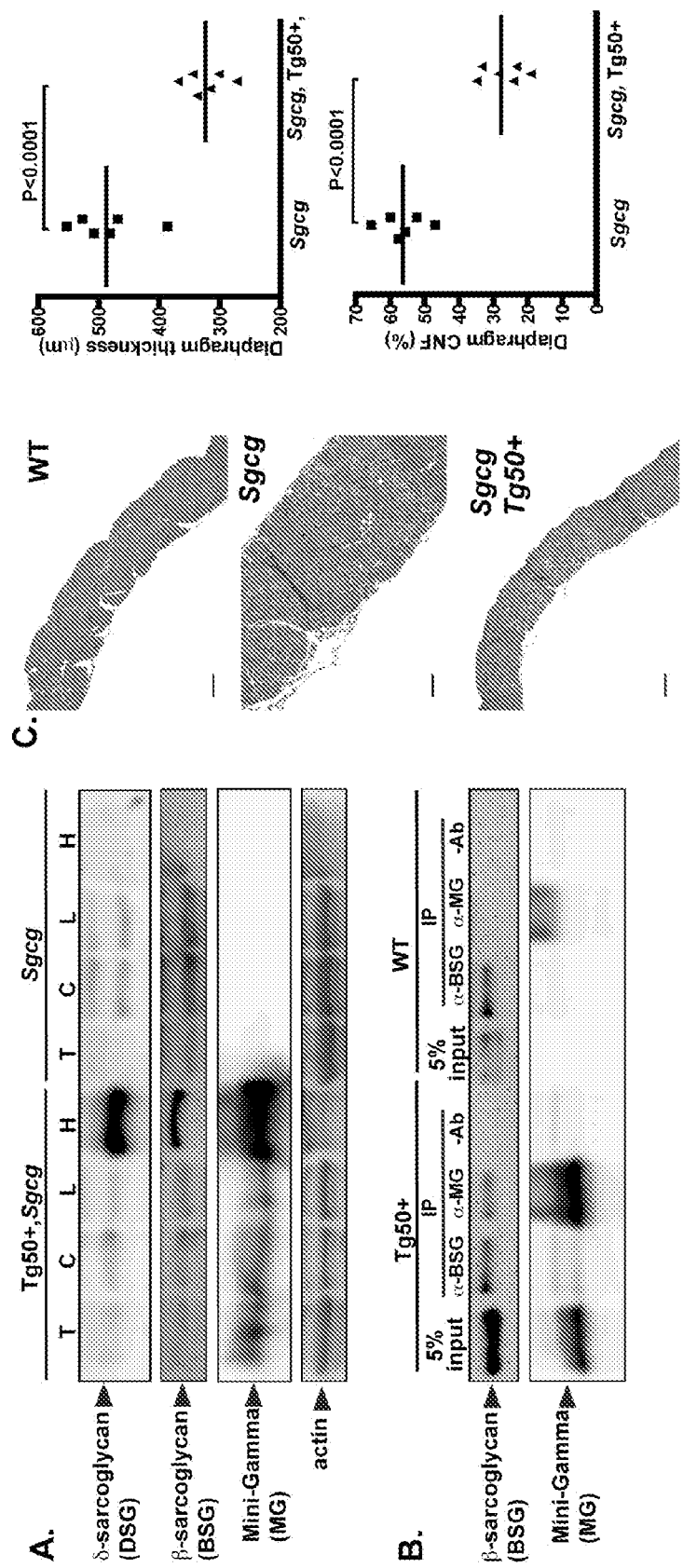
FIG. 4 shows that Mini-Gamma improved sarcoglycan trafficking and Sgcg mice skeletal muscle pathology. A. In the absence of γ-sarcoglycan, β- and δ-sarcoglycan content in the heavy microsomal fraction is reduced due to impaired sarcolemma targeting, consistent with previous reports [Hack et al., J Cell Sci 113 (Pt 14): 2535-2544 (2000)]. In Tg50/Sgcg mice, β- and δ-sarcoglycan protein levels were increased in the heavy microsomal fraction compared to those from Sgcg muscle without the Mini-Gamma transgene. B. Co-immunoprecipitation from the heavy microsomal fraction was performed to test the interaction between Mini-Gamma and other sarcoglycans in vivo. Mini-Gamma was precipitated using an antibody against β-sarcoglycan (α-BSG). The Xpress tag antibody to Mini-Gamma (α-MG) also resulted in precipitation of β-sarcoglycan. C. Mini-Gamma improved diaphragm muscle pathology in Sgcg mice. The diaphragm muscle is severely affected by the dystrophic process in Sgcg mice, as it is other mouse models of muscular dystrophy, and this is seen as marked thickening, referred to as pseudohypertrophy [Hack et al., J Cell Biol 142: 1279-1287 (1998)]. In Sgcg/Tg50 mice, the thickness of the diaphragm muscle was reduced. Central nucleation, another feature of dystrophic muscle, is increased in Sgcg mice, reflecting increased regeneration. The percentage of centrally nucleated fibers was reduced in diaphragm muscle from Sgcg/Tg50 mice compared to Sgcg mice, consistent with reduced degeneration and therefore a decreased need for regeneration. Scale bar=100 µm.

Proper assembly of sarcoglycan complex is essential for its translocation to the plasma membrane in the muscle cells. In the absence of γ-sarcoglycan, sarcolemma targeting of β- and δ-sarcoglycan is impaired, reducing β- and δ-sarcoglycan content in the heavy microsomal fraction [Hack et al., J Cell Sci 113 (Pt 14): 2535-2544 (2000)]. Tg50+ mice were crossed with Sgcg null animals to assess the capacity of Mini-Gamma to rescue the absence of Sgcg. In Sgcg/Tg50 animals, β- and δ-sarcoglycan protein levels were increased in the heavy microsomal fraction compared to those from Sgcg animals (FIG. 4A). To test the interaction between Mini-Gamma and the other sarcoglycans in vivo, co-immunoprecipitation was performed from the heavy microsomal fraction. Mini-Gamma was precipitated using an antibody specific for β-sarcoglycan BSG (FIG. 4B). The epitope tag antibody to Mini-Gamma also resulted in precipitation of β-sarcoglycan (FIG. 4B).

In many models of muscular dystrophy, the diaphragm muscle is one of the most severely involved muscles, and the diaphragm muscle is adversely impacted by the dystrophic process in Sgcg null mice with marked thickening [Hack et al., J Cell Biol 142: 1279-1287 (1998)]. In Sgcg/Tg50 mice, the thickness of the diaphragm muscle was reduced (FIG. 4C). Central nucleation is also a feature of dystrophic muscle, and the percentage of centrally nucleated fibers was reduced in diaphragm muscle from Sgcg/Tg50 mice compared to Sgcg mice (FIG. 4C) consistent with an improved phenotype from the presence of Mini-Gamma.

Mini-Gamma Reduces Fibrosis and Improves Function of Sgcg Hearts

Figure 5:
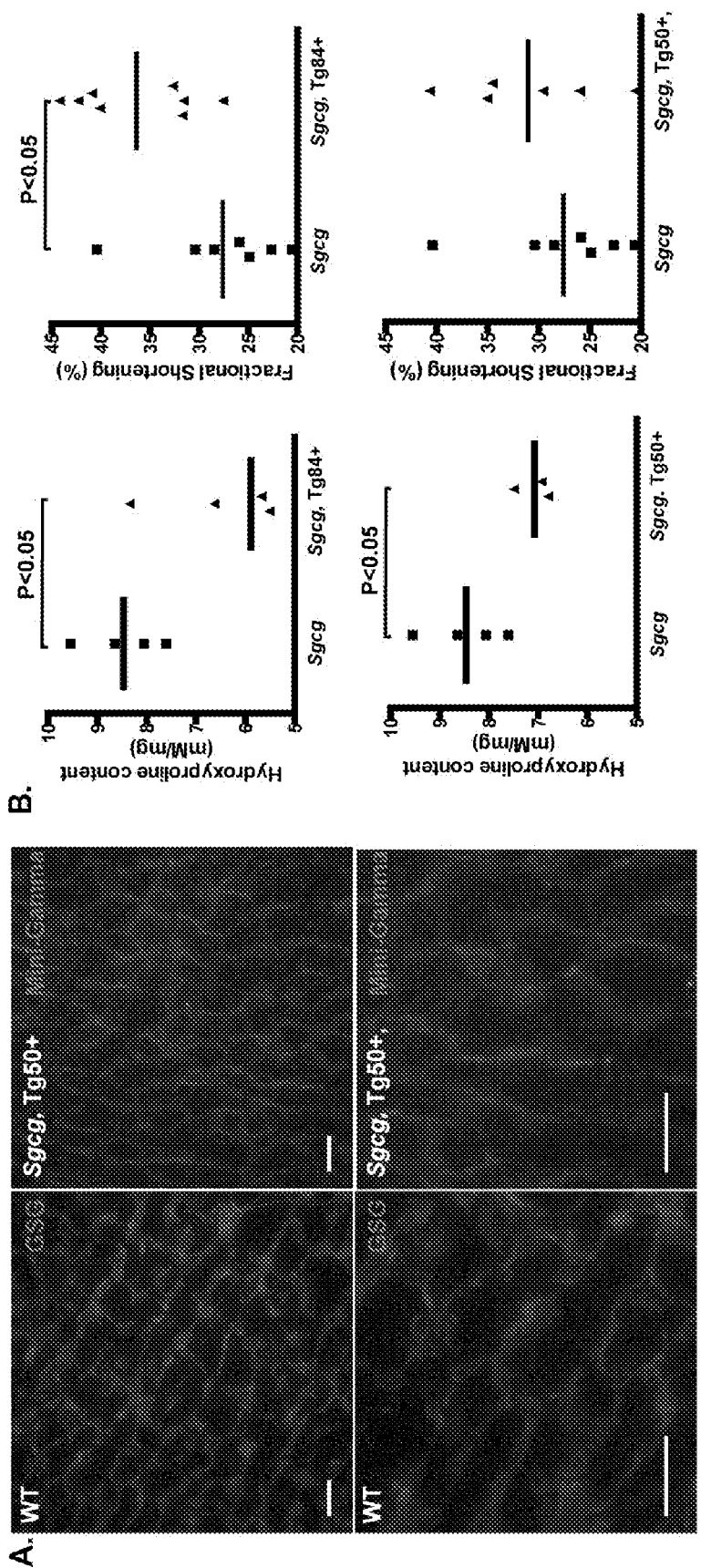
FIG. 5 shows that Mini-Gamma reduced fibrosis and improved function of Sgcg hearts. A. Mini-Gamma protein was detected at the sarcolemma of cardiomyocytes from Tg50/Sgcg mice, similar to that of the endogenous γ-sarcoglycan in wildtype animals. Scale bar=20 µm. B. Sgcg mice develop fibrosis and impaired cardiac function [Hack et al., J Cell Biol 142: 1279-1287 (1998)]. Cardiac fibrosis was monitored by hydroxyproline content. In Tg/Sgcg mice, heart fibrosis was reduced compared to Sgcg mice. Cardiac function was evaluated by echocardiography. Compared to Sgcg mice, Tg/Sgcg mice had improved fractional shortening. Fibrosis and fractional shortening measurements shown here are of males only.

Because Mini-Gamma transgenic mice also expressed protein in cardiac muscle, its expression and function in hearts were examined. Protein expressed from the Mini-Gamma transgene was detected at the sarcolemma of cardiomyocytes from Sgcg/Tg50 mice (FIG. 5A, right panels). Sgcg null mice develop cardiac dysfunction and fibrosis as they age [Hack et al., J Cell Biol 142: 1279-1287 (1998)]. Fibrosis, as monitored by hydroxyproline content, was reduced in the hearts of Sgcg/Tg mice compared to Sgcg null mice (FIG. 5B). Compared to Sgcg animals, Sgcg/Tg animals had improved fractional shortening (FIG. 5B). These data are consistent with Mini-Gamma assuming the function of full-length γ-sarcoglycan.

Example 5

Exon Skipping in LGMD 2C Myogenic Cells

Figure 6:
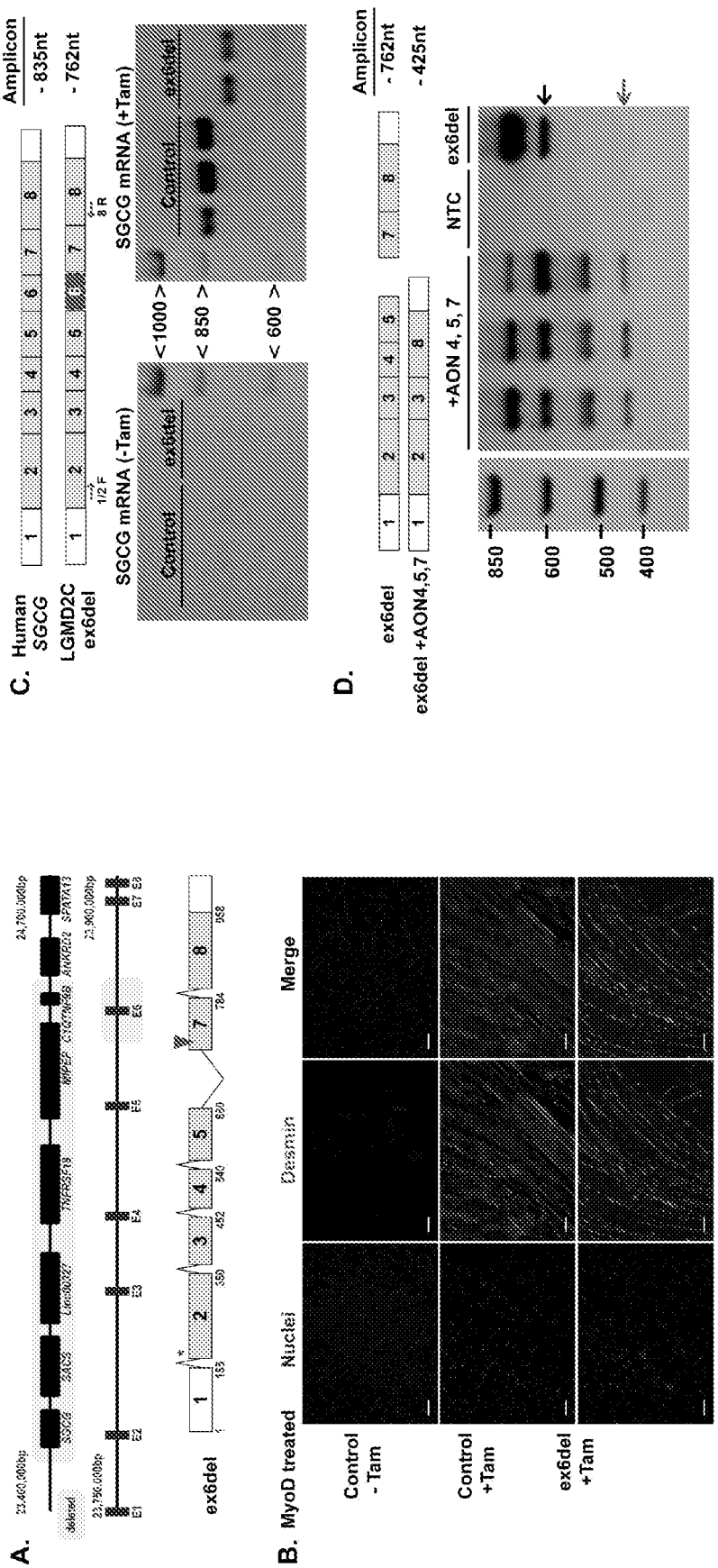
FIG. 6 depicts Antisense oligonucleotide (AON)-mediated read frame correction in human SGCG mutant cells. A. An individual with Limb Girdle Muscular Dystrophy 2C was identified as having two different deletions affecting the SGCG locus. One allele (top) harbored a 1.4 MB deletion encompassing multiple genes (shaded area). The second allele contained a smaller deletion encompassing SGCG exon 6 in its entirety (shaded area, middle schematic). Numbers refer to genome position in Genome Reference Consortium Human Build 37 (GRCh37) also known as hg19. The exon organization for exon 6 deletion (ex6del) mutant SGCG transcripts is shown in the lower schematic and this represents the SGCG transcript produced from the allele shown in the middle schematic. Numbers indicate the nucleotide number starting at exon 1. The asterisk indicates the transcription start site at position 156. The triangle indicated the premature stop codon. B. Skin fibroblasts from control and the ex6del individuals were obtained and reprogrammed to the myogenic lineage using a tamoxifen-inducible MyoD [Kimura et al., Hum Mol Genet 17: 2507-2517 (2008); Kendall et al., Science Translational Medicine 4: 164ra160 (2012)]. Desmin expression (white) and multi-nucleated myotube formation were readily seen in MyoD-transduced fibroblasts after 4OH-tamoxifen exposure (5 µM, 48 hours). Nuclei are labeled with Hoechst 3342. Scale bar=10 µM. Differentiation of ex6del fibroblasts was comparable to control. C. RT-PCR demonstrated SGCG transcripts from control and SGCG ex6del cells from reprogrammed (right) fibroblasts after differentiation (5 µM 4OH-tamoxifen, 48 hours; 12d differentiation) but not in undifferentiated reprogrammed fibroblasts. D. MyoD-reprogrammed fibroblasts were treated with AONs targeting exons 4 (SEQ ID NO: 4), 5 (SEQ ID NO: 11), and 7 (SEQ ID NO: 31) (100 nM/AON, 300 nM total). RT-PCR demonstrated the expected skipped products, including the smallest product representing exons 2, 3 and 8 and deleted for exons 4, 5, and 7 (lower arrow). Results from 3 independent replicates are shown for AON treatment. NTC=no-template control for RTPCR. Upper arrow indicates the endogenous single exon skipping of exon 7 in the ex6del SGCG transcript.

Fibroblasts were obtained from an individual with LGMD 2C. This individual carried a large deletion of 1.4 MB spanning 7 genes, including SGCG encoding γ-sarcoglycan on one allele. The other allele was deleted for 14,000 bp that encompassed only exon 6 of SGCG (FIG. 6A), leading to a premature stop codon and disrupting the reading frame (triangle). The individual has clinically diagnosed LGMD 2C with progressive muscle weakness and elevated creatine kinase (CK), which began in early childhood. A muscle biopsy confirmed reduced γ-sarcoglycan and reduction of the other sarcoglycans. Fibroblasts were obtained and induced into a myogenic lineage by expression using a tamoxifen (Tam) inducible MyoD, following similar methods used to examine DMD cells [Kimura et al., Hum Mol Genet 17: 2507-2517 (2008); Kendall et al., Science Translational Medicine 4: 164ra160 (2012)]. After induction, MyoD reprogrammed fibroblasts entered into the myogenic lineage as documented by expression of desmin and MyoD, as well as the appearance of elongated myotube-like structures (FIG. 6B). LGMD 2C fibroblasts entered into the myogenic lineage similar to control cells. SGCG RNA expression was detected in MyoD reprogrammed fibroblasts (FIG. 6C) from both control and the LGMD 2C patient (ex6del). The degree of SGCG RNA expression was qualitatively less in ex6del, consistent with only a single SGCG allele.

Figure 7:
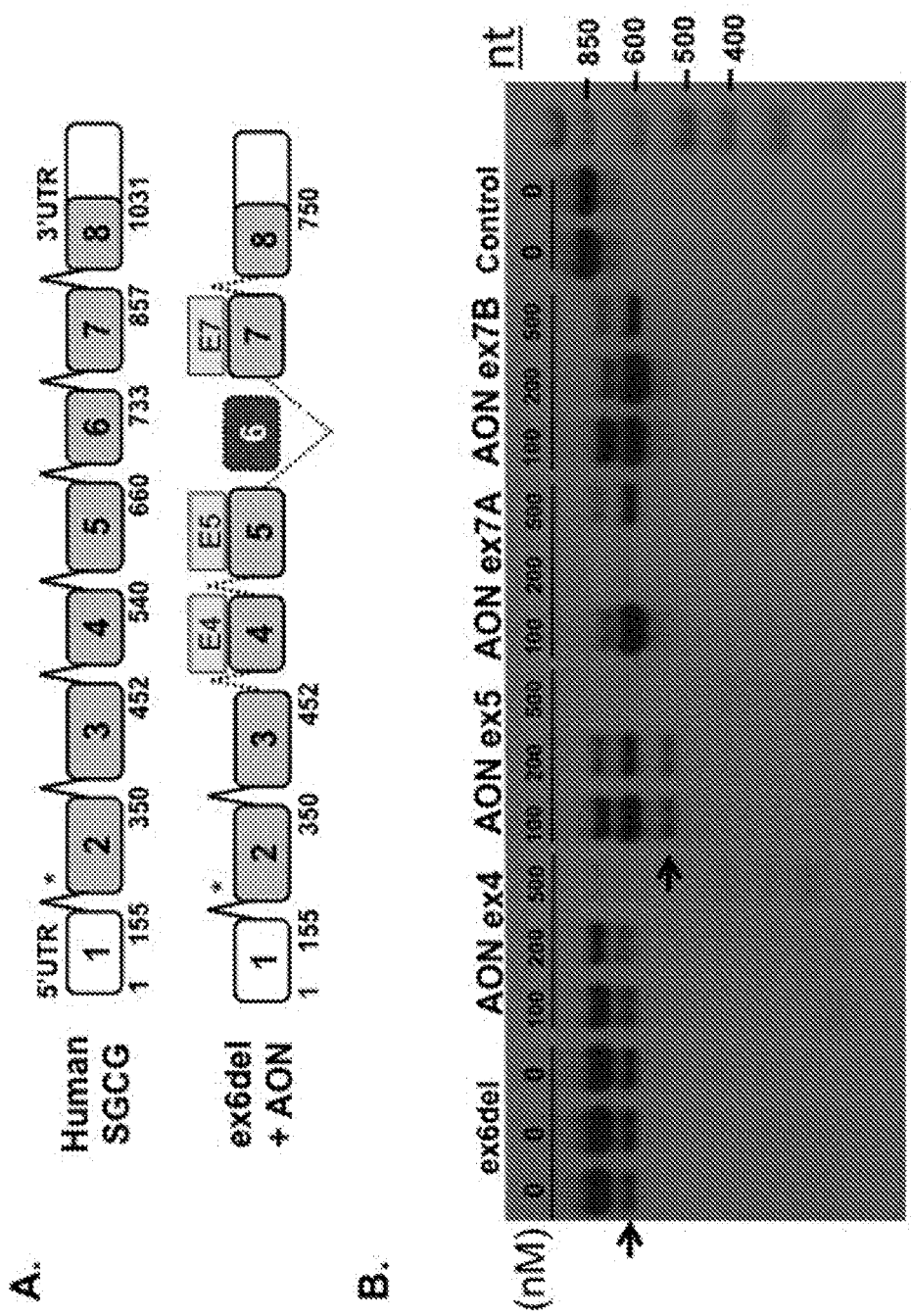
FIG. 7 depicts results using reprogrammed fibroblasts from SGCG ex6 del patient cells when skipping individual exons with AONs. A. Schematic representing the size of each exon and the position of AONs directed at exon 4 (E4), exon 5 (E5) or exon 7 (E7). This LGMD 2C patient is deleted for exon 6. B. Gel electrophoresis of RT-PCR amplified SGCG mRNA before or after exon skipping using single 2OMePS AON targeting exons 4 (SEQ ID NO: 4), 5 (SEQ ID NO: 11), or 7 (SEQ ID NOs: 31 and 33) (100-500 nM AON, 48 hours). The first three lanes represent the SGCG mRNA present ex6del cells without any AON present. Lanes 4-6 represent AON directed at exon 5 in three different concentrations, resulting in the skipping of only exon 5. Lanes 7-9 represent AON directed at exon 7 resulting in the skipping of only exon 7. Lanes 10-12 represent AON directed at exon 7 using an alternative sequence resulting in the skipping of only exon 7. The two arrows represent a small degree of exon 7 skipping SGCG mRNA that occurs in the absence of AON-induced skipping. Note, single skipped exons including skipping only 4, 5, 6 or 7 will not restore reading frame. 2OMePS transfection demonstrated dose-dependent cytotoxicity at higher AON concentrations by the 48 h time point. Fifty nanograms (ng) of cDNA template was used for control samples and 100 ng was used for ex6del samples.

AONs using 2'-O-methyl phosphorothioate (2OMePS) chemistry were targeted to intra-exonic regions in SGCG exons 4, 5, and 7, in accordance with established guidelines [Aartsma-Rus, Methods in molecular biology 867: 117-129 (2012)]. Transfection of reprogrammed ex6del cells with single 2OMePS AONs (SEQ ID NOs: 4, 11, and 29) demonstrated dose-dependency except at the highest levels where there was evidence for cellular toxicity (FIG. 7). Note that SEQ ID NO: 31 was used in the lanes marked AON ex7A, while SEQ ID NO: 33 was used in the lanes marked AON ex7B. Interestingly, there was evidence for endogenous skipping of exon 7 in the absence of AONs to exon 7 (FIG. 6C last two lanes band at 600 bp, 6D upper arrow, and FIG. 7B indicated by arrows). To generate the multi-exon skipping read frame corrected ex6del transcript, reprogrammed cells were treated with a cocktail of AONs targeting exons 4, 5, and 7 (i.e., Cocktail 1 (which consisted of SEQ ID NOs: 5, 12, 19, and 32) and Cocktail 2 (which consisted of SEQ ID NOs: 5, 12, 23, and 32) (100 nM/AON, 300 nM total; see Table 2). Analysis of PCR-amplified transcripts 3 days after treatment demonstrated the generation of an internally truncated transcript with the desired read frame correction of ex6del SGCG (FIG. 8D, marked Mini-Gamma transcript) in addition to the intermediate skipped products. Collectively, these data demonstrated the potential of correcting SGCG frameshift mutations with a multi-exon skipping AON strategy.

Exon skipping of SGCG was also tested on fibroblasts derived from a patient with an SGCG exon 7 deletion (ex7del). The ex7del mutant SGCG transcript includes the exon 6 coding region. Reprogrammed control or ex7del cells were transfected with single 2'-O-methyl phosphorothioate (2OMePS) AON or phosphorodiamidate morpholino oligonucleotides (PMO). Single AON mediated exon 6 skipping was demonstrated in the mutant ex7del cells (FIG. 8). Individual exon 6 skipping was dose-dependent in control cells, as multiple PMOs targeting exon 6 induced skipping at higher concentrations (FIG. 8). In order to generate internally truncated Mini-Gamma transcript by skipping exons 4, 5, 6, and 7, control SGCG normal cells were treated with multi-exon skipping 4-AON cocktails (Cocktail 1 (which consisted of SEQ ID NOs: 5, 12, 19, and 32) and Cocktail 2 (which consisted of SEQ ID NOs: 5, 12, 23, and 32)). FIG. 8 shows skipping using cocktails containing PMOs to skip exons 4, 5, 6 and 7 to generate the desired internally truncated Mini-Gamma transcript. These results underline the need to utilize cocktails of antisense sequences, as modest single exon skipping can be augmented when generating the read frame corrected product. Compare results with FIGS. 7 and 8.

Specific antisense oligonucleotides (AONs) contemplated by the disclosure include, but are not limited to, the oligonucleotides listed in Table 2.

DISCUSSION

The disclosure demonstrates that Mini-Gamma protein is highly capable of replacing the full-length γ-sarcoglycan in flies, mice and a heterologous cell expression system. Although this strategy removes half of γ-sarcoglycan, it retains the most functional portions of γ-sarcoglycan. γ-sarcoglycan is a type II transmembrane protein with a 37 amino acid intracellular amino-terminus, a 21 amino acid transmembrane domain and a 233 amino acid extracellular domain. The initiator methionine, entire intracellular and transmembrane domains are encoded by exon 2 and therefore remain intact in Mini-Gamma. The intracellular amino-terminus of γ-sarcoglycan contains tyrosine phosphorylation consensus sequences, and tyrosine phosphorylation is seen with cell attachment and contraction and is required for proper mechano-signalling [Yoshida et al., J Biol Chem 273:

1583-1590 (1998); Barton, Am J Physiol Cell Physiol 290: C411-419 (2006); Barton, J Biol Chem 285: 17263-17270 (2010); Spinazzola et al., gamma-sarcoglycan is required for the response of archvillin to mechanical stimulation in skeletal muscle. Hum Mol Genet (2015); Moorwood et al., Skeletal muscle 4: 13 (2014)]. The intracellular domain has also been shown to interact directly with intermediate filament protein filamin-C and actin-associated protein archvillin [Spinazzola et al., gamma-sarcoglycan is required for the response of archvillin to mechanical stimulation in skeletal muscle. Hum Mol Genet (2015); Thompson et al., J Cell Biol 148: 115-126 (2000)]. The amino-terminal half extracellular domain is important for interacting with other sarcoglycans during complex assembly [Chen et al., Exp Cell Res 312: 1610-1625 (2006). Because Mini-Gamma interacted with other sarcoglycans and translocated to the plasma membrane, suggesting that the residual extracellular portion was sufficient for membrane targeting. The carboxyl-terminal extracellular region contains an "EGF-like cysteine rich domain" that is conserved among 3-, 6- and γ-sarcoglycan and remained intact In the Mini-Gamma protein [Bonnemann et al., Nat Genet 11: 266-273 (1995); Nigro et al., Nat Genet 14: 195-198 (1996); McNally et al., Am J Hum Genet 59: 1040-1047 (1996)]. This cysteine-rich motif has been shown to form intra-molecular disulfide bridges and is required for plasma membrane targeting [Shi et al., Muscle Nerve 29: 409-419 (2004); Chen et al., Exp Cell Res 312: 1610-1625 (2006); Chan et al., J Cell Biol 143: 2033-2044 (1998)]. Missense mutations of these cysteines and small deletions in this region cause severe forms of muscular dystrophy in patients [Piccolo et al., Hum Mol Genet 5: 2019-2022 (1996); McNally et al., Hum Mol Genet 5: 1841-1847 (1996)].

The most common mutation in the SGCG gene is a frameshifting mutation in exon s6, 521ΔT [Noguchi et al., Science 270: 819-822 (1995); McNally et al., Am J Hum Genet 59: 1040-1047 (1996)]. An exon skipping strategy that includes exon 6 will benefit not only patients carrying the 521ΔT mutation, which alone accounts for about half of all LGMD2C patients, but also patients carrying missense, nonsense or frame shifting mutations spanning from exon 4 to exon 7. One concern for exon skipping strategy has been that nonsense-mediated mRNA decay (NMD) mechanism may leave little or no mRNA transcripts to work with [Baker et al., Curr Opin Cell Biol 16: 293-299 (2004)]. However, sufficient RNA for skipping was identified herein even from a single allele, suggesting that this will not be a hurdle.

What is claimed is:

1. A composition comprising two or more modified antisense oligonucleotides selected from the group consisting of oligonucleotides having a sequence as set out in SEQ ID NOs: 4-9, 11-12, 14-29, and 31-34.

2. The composition of claim 1, wherein the modified antisense oligonucleotides cannot form an RNase H substrate.

3. The composition of claim 1, wherein at least one of the modified antisense oligonucleotides comprises a modified oligonucleotide backbone.

4. The composition of claim 3, wherein the modified oligonucleotide backbone comprises a modified moiety substituted for the sugar of at least one of the oligonucleotides.

5. The composition of claim 4, wherein the modified moiety is a Morpholino.

6. The composition of claim 3, wherein the modified oligonucleotide backbone of at least one of the oligonucleotides comprises at least one modified internucleotide linkage.

7. The composition of claim 6, wherein the modified internucleotide linkage is a tricyclo-DNA (tc-DNA) modification.

8. The composition of claim 6, wherein the modified internucleotide linkage comprises a modified phosphate.

9. The composition of claim 8, wherein the modified phosphate is selected from the group consisting of a methyl phosphonate, a methyl phosphorothioate, a phosphoromorpholidate, a phosphoropiperazidate and a phosphoroamidate.

10. The composition of claim 3, wherein at least one of the modified antisense oligonucleotides is a 2'-O-methyl-oligoribonucleotide.

11. The composition of claim 1, wherein at least one of the modified antisense oligonucleotides comprises a peptide nucleic acid.

12. The composition of claim 1, wherein at least one of the modified antisense oligonucleotides is chemically linked to one or more conjugates that enhance the activity, cellular distribution, or cellular uptake of the antisense oligonucleotide.

13. The composition of claim 12, wherein at least one of the modified antisense oligonucleotides is chemically linked to a polyethylene glycol molecule.

14. The composition of claim 12 wherein the conjugate is a peptide that enhances cellular uptake.

15. The composition of claim 14 wherein the peptide is selected from the group consisting of a nuclear localization signal (NLS), HIV-1 TAT protein, a peptide comprising an integrin binding domain, oligolysine, adenovirus fiber protein and a peptide comprising a receptor-mediated endocytosis (RME) domain.

16. A pharmaceutical composition, comprising the composition of claim 1 and a physiologically compatible buffer.

17. A method of inducing exon-skipping of a gamma sarcoglycan RNA, comprising delivering to a cell the composition of claim 1, thereby inducing exon-skipping of the gamma sarcoglycan RNA.

18. The method of claim 17, wherein the cell is a human muscle cell.

19. The method of claim 18, wherein the human muscle cell is in a patient.

20. The method of claim 19, wherein the patient has muscular dystrophy.

21. The method of claim 20, wherein the muscular dystrophy is Limb Girdle Muscular Dystrophy type 2C (LGMD2C).

* * * * *

UNITED STATES PATENT AND TRADEMARK OFFICE
CERTIFICATE OF CORRECTION

| | | |
|---|---|---|
| PATENT NO. | : 10,801,029 B2 | Page 1 of 1 |
| APPLICATION NO. | : 16/395741 | |
| DATED | : October 13, 2020 | |
| INVENTOR(S) | : Elizabeth McNally et al. | |

It is certified that error appears in the above-identified patent and that said Letters Patent is hereby corrected as shown below:

On the Title Page

At item (57), Line 7, "dystrophy." should be -- dystrophy, --.

Signed and Sealed this
Eighth Day of June, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 36

<210> SEQ ID NO 1
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 1
cgaattcacc atggatctgt acgacga                                        27

<210> SEQ ID NO 2
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 2
ctagatgcat gctcgagtca aagacag                                        27

<210> SEQ ID NO 3
<211> LENGTH: 148
<212> TYPE: DNA
<213> ORGANISM: Artificial Sequence
<220> FEATURE:
<223> OTHER INFORMATION: Synthetic Polynucleotide

<400> SEQUENCE: 3
attttgcaaa ttttataaat ctctttctag gactcatctc tgcttctaca atcaacccag    60
aatgtgactg taaatgcgcg caactcagaa ggggaggtca caggcaggtt aaaagtcggt   120
gagtccagct tcatcatggt gctttgca                                      148

<210> SEQ ID NO 4
<211> LENGTH: 25
<212> TYPE: DNA
<213> ORGANISM: Artificial Sequence
<220> FEATURE:
```

```
<223> OTHER INFORMATION: Synthetic Polynucleotide

<400> SEQUENCE: 4
agucacauuc uggguugauu guaga                                              25

<210> SEQ ID NO 5
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 5
agtcacattc tgggttgatt gtaga                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 6
ccugugaccu ccccuucuga guugc                                              25

<210> SEQ ID NO 7
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 7
cctgtgacct ccccttctga gttgc                                              25

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 8
gcaccaugau gaagcuggac ucacc                                              25

<210> SEQ ID NO 9
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 9
gcaccatgat gaagctggac tcacc                                              25

<210> SEQ ID NO 10
<211> LENGTH: 179
<212> TYPE: DNA
<213> ORGANISM: Artificial Sequence
<220> FEATURE:
<223> OTHER INFORMATION: Synthetic Polynucleotide

<400> SEQUENCE: 10
gtttataata aactgtttta attcttcagg tcccaaaatg gtagaagtcc agaatcaaca        60
gtttcagatc aactccaacg acggcaagcc actatttact gtagatgaga aggaagttgt       120
```

```
ggttggtaca gataaacttc gagtaactgg tatgtactaa ctcgagaaaa acacaacat      179
```

<210> SEQ ID NO 11
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 11

```
cugaaacugu ugauucugga cuucu                                          25
```

<210> SEQ ID NO 12
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 12

```
ctgaaactgt tgattctgga cttct                                          25
```

<210> SEQ ID NO 13
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 13

```
tcctgataca tctttgtttt tgtttaggg cctgaagggg ctcttttga acattcagtg       60 gagacacccc ttgtcagagc cgacccgttt caagaccta ggtaagaatt tttgttcaaa     120
tattaacaac c                                                         131
```

<210> SEQ ID NO 14
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 14

```
agccccuuca ggcccuaaac aaaaaacaa                                      29
```

<210> SEQ ID NO 15
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 15

```
agccccttca ggccctaaac aaaaaacaa                                      29
```

<210> SEQ ID NO 16
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 16

```
agccccuuca ggcccuaaac aaaaa                                          25
```

```
<210> SEQ ID NO 17
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 17
agccccttca ggccctaaac aaaaa                                    25

<210> SEQ ID NO 18
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 18
auguucaaaa agagccccuu caggc                                    25

<210> SEQ ID NO 19
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 19
atgttcaaaa agagcccctt caggc                                    25

<210> SEQ ID NO 20
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 20
aauguucaaa agagccccuu caggcc                                   26

<210> SEQ ID NO 21
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 21
aatgttcaaa agagcccctt caggcc                                   26

<210> SEQ ID NO 22
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 22
cuccacugaa uguucaaaaa gagcc                                    25

<210> SEQ ID NO 23
<211> LENGTH: 25
<212> TYPE: DNA
<213> ORGANISM: Artificial Sequence
<220> FEATURE:
<223> OTHER INFORMATION: Synthetic Polynucleotide
```

```
<400> SEQUENCE: 23
ctccactgaa tgttcaaaaa gagcc                                          25

<210> SEQ ID NO 24
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 24
ucuccacuga auguucaaaa gagccc                                         26

<210> SEQ ID NO 25
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 25
tctccactga atgttcaaaa gagccc                                         26

<210> SEQ ID NO 26
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 26
gggugucucc acugaauguu caaa                                           24

<210> SEQ ID NO 27
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 27
gggtgtctcc actgaatgtt caaa                                           24

<210> SEQ ID NO 28
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 28
gucuugaaac gggucggcuc ugaca                                          25

<210> SEQ ID NO 29
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 29
gtcttgaaac gggtcggctc tgaca                                          25

<210> SEQ ID NO 30
```

<211> LENGTH: 184
<212> TYPE: DNA
<213> ORGANISM: Artificial Sequence
<220> FEATURE:
<223> OTHER INFORMATION: Synthetic Polynucleotide

<400> SEQUENCE: 30

```
ttttttttgt gcttcttttc ctcatctcag attagaatcc cccactcgga gtctaagcat    60
ggatgcccca aggggtgtgc atattcaagc tcacgctggg aaaattgagg cgctttctca   120
aatggatatt cttttcata gtagtgatgg aatggtgagt tcattcacag atcagcctcc   180
tact                                                               184
```

<210> SEQ ID NO 31
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 31

```
ggcauccaug cuuagacucc gagug                                          25
```

<210> SEQ ID NO 32
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 32

```
ggcatccatg cttagactcc gagtg                                          25
```

<210> SEQ ID NO 33
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 33

```
cucaccauuc caucacuacu augaa                                          25
```

<210> SEQ ID NO 34
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 34

```
ctcaccattc catcactact atgaa                                          25
```

<210> SEQ ID NO 35
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 35

```
tctaagatgg tgcgtgagca g                                              21
```

<210> SEQ ID NO 36
<211> LENGTH: 20

```
<212> TYPE: DNA
<213> ORGANISM: Artificial Sequence
<220> FEATURE:
<223> OTHER INFORMATION: Synthetic Polynucleotide

<400> SEQUENCE: 36
gccacagaca ggtacagctt                                              20
```